(12) United States Patent
Günther et al.

(10) Patent No.: US 11,278,503 B2
(45) Date of Patent: Mar. 22, 2022

(54) PHARMACEUTICAL COMPOSITIONS COMPRISING SEMIFLUORINATED ALKANES FOR THE TREATMENT OF CONTACT LENSE-RELATED CONDITIONS

(71) Applicant: NOVALIQ GMBH, Heidelberg (DE)

(72) Inventors: Bernhard Günther, Dossenheim (DE); Markus Beier, Weinheim (DE); Oliver Schlüter, Mannheim (DE)

(73) Assignee: NOVALIQ GMBH, Heidelberg (DE)

( * ) Notice: Subject to any disclaimer, the term of this patent is extended or adjusted under 35 U.S.C. 154(b) by 175 days.

(21) Appl. No.: 16/612,961

(22) PCT Filed: May 9, 2018

(86) PCT No.: PCT/EP2018/062027
§ 371 (c)(1),
(2) Date: Nov. 12, 2019

(87) PCT Pub. No.: WO2018/206656
PCT Pub. Date: Nov. 15, 2018

(65) Prior Publication Data
US 2020/0060987 A1 Feb. 27, 2020

(30) Foreign Application Priority Data

May 12, 2017 (EP) .................... 17170826

(51) Int. Cl.
*A61K 31/02* (2006.01)
*A61P 27/04* (2006.01)
*A61K 9/00* (2006.01)
*A61K 9/08* (2006.01)

(52) U.S. Cl.
CPC ............ *A61K 31/02* (2013.01); *A61K 9/0048* (2013.01); *A61K 9/08* (2013.01); *A61P 27/04* (2018.01)

(58) Field of Classification Search
CPC .................................................. A61K 31/02
See application file for complete search history.

(56) References Cited

U.S. PATENT DOCUMENTS

| | | | |
|---|---|---|---|
| 2,616,927 A | 11/1952 | Kauck et al. |
| 5,077,036 A | 12/1991 | Long |
| 5,326,566 A | 7/1994 | Parab |
| 5,336,175 A | 8/1994 | Mames |
| 5,370,313 A | 12/1994 | Beard |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers et al. |
| 5,980,936 A | 11/1999 | Krafft et al. |
| 5,981,607 A | 11/1999 | Ding et al. |
| 6,042,845 A | 3/2000 | Sun et al. |
| 6,060,085 A | 5/2000 | Osborne |
| 6,113,919 A | 9/2000 | Cronelus |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,335,335 B2 | 1/2002 | Higashiyama et al. |
| 6,372,243 B2 | 4/2002 | Kobuch |
| 6,391,879 B1 | 5/2002 | Reeves |
| 6,458,376 B1 | 10/2002 | Meadows |
| 6,486,212 B2 | 11/2002 | Meinert |
| 6,489,367 B1 | 12/2002 | Meinert |
| 6,576,663 B2 | 6/2003 | Klimko |
| 6,730,328 B2 | 5/2004 | Maskiewicz et al. |
| 7,001,607 B1 | 2/2006 | Menz et al. |
| 7,026,359 B1 | 4/2006 | Gross |
| 7,258,869 B1 | 8/2007 | Berry et al. |
| 7,740,875 B2 | 6/2010 | Dechow |

(Continued)

FOREIGN PATENT DOCUMENTS

| CN | 200977281 Y | 11/2007 |
|---|---|---|
| CN | 202136470 U | 2/2012 |

(Continued)

OTHER PUBLICATIONS

Bardin et al., "Long-Range Nanometer-Scale Organization of Semifluorinated Alkane Monolayers at the Air/Water Interface," Langmuir, 2011, 27, 13497-13505.

Blackie et al., "MGD: Getting to the Root Cause of Dry Eye", Review of Optometry, 2012, pp. 1-12.

Broniatowski, M. et al., "Langmuir Monolayers Characteristics of (Perfluorodecyl)-Alkanes," Journal of Physical Chemistry B, 2004, 108, 13403-13411.

Chhadva et al., "Meibomian Gland Disease The Role of Gland Dysfunction in Drye Eye Disease," Ophthalmology (2017) 124(11 Supplement): S20-S26.

Costa Gomes et al., "Solubility of dioxygen in seven fluorinated liquids," Journal of Fluorine Chemistry, 2004, 125, 1325-1329.

Davies, N., "Biopharmaceutical Considerations in Topical Ocular Drug Delivery," Clinical and Experimental Pharmacology and Physiology, 2000, 27, 558-562.

(Continued)

*Primary Examiner* — Paul V Ward
(74) *Attorney, Agent, or Firm* — Hoxie & Associates LLC

(57) ABSTRACT

A pharmaceutical composition comprising a semifluorinated alkane of formula (I): $F(CF2)_n(CH2)_mH$, wherein n is an integer from 4 to 6, and m is an integer from 5 to 8, for use in the treatment or prevention of a disease or condition relating to an ocular surface of an eye of an individual, wherein the individual is a contact lens wearer, and wherein the contact lens is a hydro gel contact lens and the composition is administered topically to a surface of the eye of the individual before the contact lens is inserted to the eye of the individual and/or during contact lens wear and/or after the contact lens has been removed from the eye of the individual, or wherein the contact lens is a silicone hydrogel contact lens and the composition is administered topically to a surface of the eye of the individual after the contact lens has been removed from the eye of the individual.

9 Claims, No Drawings

(56) References Cited

U.S. PATENT DOCUMENTS

| | | |
|---|---|---|
| 8,029,977 B2 | 10/2011 | Meinert et al. |
| 8,222,292 B2 | 7/2012 | Goskonda et al. |
| 8,470,873 B2 | 6/2013 | Chen |
| 8,614,178 B2 | 12/2013 | Theisinger et al. |
| 8,796,340 B2 | 8/2014 | Theisinger et al. |
| 8,916,157 B2 | 12/2014 | Krause et al. |
| 8,986,738 B2 | 3/2015 | Meinert |
| 9,241,900 B2 | 1/2016 | Wilson |
| 9,308,262 B2 | 4/2016 | Günther et al. |
| 9,757,459 B2 | 9/2017 | Theisinger et al. |
| 9,757,460 B2 | 9/2017 | Günther et al. |
| 9,770,508 B2 | 9/2017 | Günther et al. |
| 10,045,996 B2 | 8/2018 | Theisinger et al. |
| 10,507,132 B2 | 12/2019 | Graf et al. |
| 2002/0004063 A1 | 1/2002 | Zhang |
| 2002/0128527 A1 | 9/2002 | Meinert |
| 2003/0018044 A1 | 1/2003 | Peyman |
| 2003/0027833 A1 | 2/2003 | Cleary et al. |
| 2003/0170194 A1 | 9/2003 | Piotrowiak |
| 2004/0044045 A1 | 3/2004 | Burk |
| 2004/0082660 A1 | 4/2004 | Ueno |
| 2004/0265362 A1 | 12/2004 | Susilo |
| 2004/0266702 A1 | 12/2004 | Dawson et al. |
| 2005/0079210 A1 | 4/2005 | Gupta |
| 2005/0175541 A1 | 8/2005 | Lanza et al. |
| 2005/0274744 A1 | 12/2005 | Spada et al. |
| 2005/0288196 A1 | 12/2005 | Horn |
| 2006/0153905 A1 | 7/2006 | Carrara et al. |
| 2008/0050335 A1 | 2/2008 | Faour et al. |
| 2008/0153909 A1 | 6/2008 | Dana et al. |
| 2008/0207537 A1 | 8/2008 | Turner et al. |
| 2008/0234389 A1 | 9/2008 | Mecozzi et al. |
| 2008/0260656 A1 | 10/2008 | Mallard |
| 2009/0149546 A1 | 6/2009 | Chang |
| 2010/0006600 A1 | 1/2010 | Dascanio |
| 2010/0008996 A1 | 1/2010 | Meinert |
| 2010/0016814 A1 | 1/2010 | Gokhale et al. |
| 2010/0137252 A1 | 6/2010 | Matsumura et al. |
| 2010/0149546 A1 | 6/2010 | Kobayashi et al. |
| 2010/0226997 A1 | 9/2010 | Bowman et al. |
| 2010/0274215 A1 | 10/2010 | Wong et al. |
| 2010/0310476 A1 | 12/2010 | Tamarkin et al. |
| 2011/0269704 A1 | 11/2011 | Seigfried |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2012/0244177 A1 | 9/2012 | Theisinger et al. |
| 2013/0011484 A1 | 1/2013 | Bevier |
| 2013/0046014 A1 | 2/2013 | Theisinger et al. |
| 2013/0084250 A1 | 4/2013 | Hagedorn et al. |
| 2013/0266652 A1 | 10/2013 | Theisinger et al. |
| 2013/0303473 A1 | 11/2013 | Wilson |
| 2013/0336557 A1 | 12/2013 | Cruzat et al. |
| 2014/0004197 A1 | 1/2014 | Theisinger et al. |
| 2014/0100180 A1 | 4/2014 | Gunther et al. |
| 2014/0140942 A1 | 5/2014 | Gunther et al. |
| 2014/0186350 A1 | 7/2014 | Ghosh et al. |
| 2014/0303219 A1 | 10/2014 | Bingaman et al. |
| 2014/0369993 A1 | 12/2014 | Gunther et al. |
| 2015/0045282 A1 | 2/2015 | Elsohly et al. |
| 2015/0224064 A1 | 8/2015 | Günther et al. |
| 2015/0238605 A1 | 8/2015 | Günther et al. |
| 2016/0101178 A1 | 4/2016 | Wilson |
| 2016/0159902 A1 | 6/2016 | Günther et al. |
| 2016/0243189 A1 | 8/2016 | Gu et al. |
| 2017/0020726 A1 | 1/2017 | Labombarbe et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2018/0360908 A1 | 12/2018 | Beier et al. |
| 2019/0274970 A1 | 9/2019 | Gunther et al. |
| 2019/0321218 A1 | 10/2019 | Graf et al. |
| 2019/0328717 A1 | 10/2019 | Günther et al. |
| 2019/0343793 A1 | 11/2019 | Günther et al. |
| 2020/0023035 A1 | 1/2020 | Löscher et al. |

FOREIGN PATENT DOCUMENTS

| | | | |
|---|---|---|---|
| CN | 203524843 U | 4/2014 | |
| EP | 0089815 | 9/1983 | |
| EP | 0593552 | 4/1994 | |
| EP | 0670159 | 9/1995 | |
| EP | 0 939 655 | 6/2002 | |
| EP | 1 152 749 | 4/2006 | |
| JP | S6452722 | 2/1989 | |
| JP | 2001/158734 | 6/2001 | |
| JP | 2008/505177 | 2/2008 | |
| JP | 2011/006348 | 1/2011 | |
| JP | 2011/024841 A | 2/2011 | |
| WO | WO 1995/033447 | 12/1995 | |
| WO | WO 96/40052 | 12/1996 | |
| WO | WO 1998/005301 | 12/1998 | |
| WO | WO 00/10531 | 3/2000 | |
| WO | WO 00/024376 | 5/2000 | |
| WO | WO 00/054588 | 9/2000 | |
| WO | WO 2002/049631 | 6/2002 | |
| WO | WO 2005/018530 | 3/2005 | |
| WO | WO 2005/099718 | 10/2005 | |
| WO | WO 2005/099752 | 10/2005 | |
| WO | WO 2005/123035 | 12/2005 | |
| WO | WO 2006/007510 | 1/2006 | |
| WO | WO 2006/042059 | 4/2006 | |
| WO | WO 2006/048242 | 5/2006 | |
| WO | WO 2007/008666 | 1/2007 | |
| WO | WO2007/008666 * | 1/2007 | ............... A61K 9/00 |
| WO | WO 2007/052288 | 5/2007 | |
| WO | WO 2008/019146 | 2/2008 | |
| WO | WO 2008/060359 | 5/2008 | |
| WO | WO 2009/013435 | 1/2009 | |
| WO | WO 2009/065565 | 5/2009 | |
| WO | WO 2010/062394 | 6/2010 | |
| WO | WO 2010/146536 | 12/2010 | |
| WO | WO 2011/009436 | 1/2011 | |
| WO | WO 2012/121754 | 9/2012 | |
| WO | WO 2014/041055 | 3/2014 | |
| WO | WO 2014/154531 | 10/2014 | |
| WO | WO 2015/053829 | 4/2015 | |
| WO | WO 2015/074137 | 5/2015 | |
| WO | WO 2016/025560 | 2/2016 | |
| WO | WO 2016/109531 | 7/2016 | |
| WO | WO 2018/206656 | 11/2018 | |

OTHER PUBLICATIONS

Dembinski, R. et al., "Semi-fluorinated Alkanes as Carriers for Drug Targeting in Acute Respiratory Failure," Experimental Lung Research, 2010, 36, 499-507.

Dias et al., "Solubility of oxygen in liquid perfluorocarbons," Fluid Phase Equilibria, 2004, 222-223:325-330.

Dutescu et al., "Semifluorinated alkanes as a liquid drug carrier system for topical ocular drug delivery," European Journal of Pharmaceutics and Biopharmaceutics, 2014, 88(1):123-128, Abstract Only (2 pages).

English-language machine translation of EP0670159 (A1) issued in U.S. Appl. No. 14/122,025 on Apr. 1, 2015, 10 pages.

"EvoTears—Gebrauchsanweisung," May 2015, retrieved from the Internet, date retrieved: Jun. 26, 2018, 2 pages, URL: http://video.apo-rot.de/docs/11213615.pdf.

Freiburger Dokumentenserver (FreiDok), Albert-Ludwigs-Unversität Freiburg, retrieved from http://www.freidok.uni-freiburg.de/volltexte/5682/, retrieved on Feb. 5, 2014, 2 pages.

Gayton, J., "Etiology, Prevalence, and Treatment of Dry Eye Disease," Clinical Ophthalmology, 2009, 3, 405-412.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(319), Abstract Only (2 pages).

Gehlsen, U., et al., "Omega-3 Fatty Acids Using F6H8-Carrier as Topical Therapy in Experimental Dry-Eye Disease," Investigative

(56) References Cited

OTHER PUBLICATIONS

Ophthalmology & Visual Science, 2016, 57:417, Abstract Only (1 page).
German, E.J., et al., "Reality of drop size from multi-dose eye drop bottles: is it cause for concern?" Eye, 1999, 13:93-100.
Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf (retrieved on Oct. 10, 2011).
Hardung, H., "Semifluorierte und perfluorierte Verbindungen zur topischen und parenteralen Anwendung," 2008, English Language Abstract, 2 pages, retrieved from https://freidok.uni-freiburg.de/data/5682 (retrieved on Jul. 10, 2017).
Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.
Holm, R. et al., "A novel excipient, 1-perfluorohexyloctane shows limited utility for the oral delivery of poorly water-soluble drugs," European Journal of Pharmaceutical Sciences, 2011, 42: 416-422.
International Preliminary Report on Patentability for International Application No. PCT/EP2013/068882 dated Mar. 17, 2015, 5 pages.
International Preliminary Report on Patentability for International Application No. PCT/EP2013/068909 dated Mar. 17, 2015, 7 pages.
International Preliminary Report on Patentability dated Dec. 25, 2018, for International Application No. PCT/EP2017/065163, 6 pages.
International Preliminary Report on Patentability dated Mar. 26, 2019, for International Application No. PCT/EP2017/074079, 7 pages.
International Preliminary Report on Patentability and Written Opinion for International Application No. PCT/EP2017/083770 dated Jun. 25, 2019, 7 pages.
International Preliminary Report on Patentability and Written Opinion for International Application No. PCT/EP2018/062027 dated Nov. 12, 2019, 7 pages.
International Search Report for International Application No. PCT/EP2013/068882 dated Oct. 30, 2013, 4 pages.
International Search Report for International Application No. PCT/EP2013/068909 dated Dec. 5, 2013, 4 pages.
International Search Report for International Application No. PCT/EP2017/065163, dated Aug. 8, 2017, 3 pages.
International Search Report for International Application No. PCT/EP2017/074079 dated Dec. 22, 2017, 4 pages.
International Search Report for International Application No. PCT/EP2017/083770 (revised version) dated Jul. 6, 2018, 4 pages.
International Search Report and Written Opinion for International Application No. PCT/EP2017/083770 dated Jul. 6, 2018, 14 pages.
International Search Report for International Application No. PCT/EP2018/062027 dated Jul. 6, 2018, 4 pages.
JPS6452722, English Machine Translation of the Abstract, Description, and Claims, Espacenet, Date Accessed: Feb. 10, 2016, 4 pages.
Kaercher et al., "NovaTears® as new Therapy in Dry Eye Results from three prospective, multicenter, non-interventional studies in different patient populations", TFOS Conference (Tear Film & Ocular Surface), Sep. 7-10, 2016, Montpellier, France, Poster Session II, Poster No. 60, 1 page.
Kociok, N., et al, "Influence on Membrane-Mediated Cell Activation by Vesicles of Silicone Oil or Perfluorohexyloctane," Graefe's Archive for Clinical and Experimental Ophthalmology, 2005, 243, 345-358.
Lallemand et al., "Cyclosporine A delivery to the eye: a pharmaceutical challenge," European Journal of Pharmaceutics and Biopharmaceutics, 2003, 56(3):307-318, Abstract Only (1 page).
Lemp, M., "Management of Dry Eye Disease," The American Journal of Managed Care, 2008, 14 (3), S88-S101.
Lin, H. et al., "Dry eye disease: A review of diagnostic approaches and treatments," Saudi Journal of Ophthalmology, 2014, 28:173-181.
Mackiewicz, J. et al., "In Vivo Retinal Tolerance of Various Heavy Silicone Oils," Investigative Ophthalmology & Visual Science, 2007, 48 (4), 1873-1883.
Meinert, H. et al., "Semifluorinated Alkanes—A New Class of Compounds with Outstanding Properties for Use in Ophthalmology," European Journal of Ophthalmology, 2000, 10 (3), 189-197.
Meinert, H. et al., "The Use of Semifluorinated Alkanes in Blood-Substitutes," Biomaterials, Artificial Cells, and Immobilization Biotechnology, 1993, 21 (5), 583-595.
Messmer, E.M., "The Pathophysiology, Diagnosis, and Treatment of Dry Eye Disease," (2015) Deutsches Arzteblatt International, 112(5):71-82.
Messmer, et al. "Semifluorierte Alkane als Therapie bei Meibomdrüsen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.
Messmer, et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Ophthalmologe, Aug. 2016 Poster No. PSa03-02, English Translation of Abstract, p. 138.
O'Rourke, M. et al., "Enhancing Delivery of Topical Ocular Drops," Cataract & Refractive Surgery Today Europe, 2016, 2 pages.
Perry, H., "Dry Eye Disease: Pathophysiology, Classification, and Diagnosis," The American Journal of Managed Care, 2008, 14 (3), S79-S87.
Pflugfelder et al., "The Pathophysiology of Dry Eye Disease What We Know and Future Directions for Research," Ophthalmology (2017) 124(11 Supplement): S4-S13.
Pflugfelder et al., "Treatment of Blepharitis: Recent Clinical Trials," 2014, 12(4):273-284, Abstract Only (2 pages).
Plassmann, M. et al., "Trace Analytical Methods for Semifluorinated n-Alkanes in Snow, Soil, and Air," Analytical Chemistry, 2010, 82(11), 4551-4557.
Plassmann, M. et al., "Theoretical and Experimental Simulation of the Fate of Semifluorinated n-Alkanes During Snowmelt," Environmental Science & Technology, 2010, 44 (17), 6692-6697.
Sall, K. et al. "Two Multicenter, Randomized Studies of the Efficacy and Safety of Cyclosporine Ophthalmic Emulsion in Moderate to Severe Dry Eye Disease," Ophthalmology, 2000, 107(4):631-639.
Schmutz et al., "Fluorinated Vesicles Made from Combinations of Phospholipids and Semifluorinated Alkanes. Direct Experimental Evidence of the Location of the Semifluorinated Alkane within the Bilayer", Langmuir, 2003, 19:4889-4894.
Schnetler et al., "Lipid composition of human meibum: a review", S Afr Optom, 2013, 72(2), 86-93.
Spöler et al., "Towards a New in vitro Model of Dry Eye: The ex vivo Eye Irritation Test", Developments in Ophthalmology, 2010, 45, 93-107.
Steven, P. et al. "Semifluorinated Alkane Eye Drops for Treatment of Dry Eye Disease—A Prospective, Multicenter Noninterventional Study," Journal of Ocular Pharmacology and Therapeutics (2015) vol. 31(8):498-503.
Steven, P. et al. "Semifluorinated Alkane Eye Drops for Treatment of Dry Eye Disease—A Prospective, Multicenter Noninterventional Study," Investigative Ophthalmology & Visual Science, 2015, 56:4493, Abstract Only (1 page).
Steven et al., "Semifluorinated Alkane Eye Drops for Treatment of Dry Eye Disease Due to Meibomian Gland Disease," Journal of Ocular Pharmacology and Therapeutics, 2017, 33(9):1-8.
Tiffany, J.M., "Individual Variations in Human Meibomian Composition", Exp. Eye Res., 1978, 27, 289-300.
Troiano et al., "Effect of Hypotonic .4% Hyaluronic Acid Drops in Dry Eye Patients: A Cross-Study", 2008, Cornea 27(10), 1126-1130 (Abstract Only).

(56) References Cited

OTHER PUBLICATIONS

Wirta, David L. et al., "A Clinical Phase II Study to Assess Efficacy, Safety and Tolerability of Waterfree Cyclosporine Formulation for the Treatment of Dry Eye Disease," *Ophthalmology*, 2019, 126:792-800.
Wong, D. et al., "Perfluorocarbons and Semifluorinated Alkanes," Seminars in Ophthalmology, 2000, 15 (1), 25-35.
Zhang et al., "Surface micelles of semifluorinated alkanes in Langmuir-Blodgett monolayers," Phys. Chem. Chem. Phys., 2004, 6, 1566-1569.
Agrahari, et al., "A comprehensive insight on ocular pharmacokinetics," Drug Delivery and Translational Research, 6(6):735-754 (2016).
Ahmed, et al., "Disposition of Timolol and Inulin in the Rabbit Eye Following Corneal Versus Non-Corneal Absorption," International Journal of Pharmaceutics, 1987, 38:9-21.
Baerdemaeker, "Pharmacokinetics in Obese Patients," Continuing Education in Anesthesia, Critical Care & Pain, 2004, 4:152-155.
Barata-Vallejo et al., "$(Me_3Si)_3SiH$-Mediated Intermolecular Radical Perfluoroalkylation Reactions of Olefins in Water," J. Org. Chem., 2010, 75:6141-6148.
Bertilla et al., "Semifluorinated Alkanes as Stabilizing Agents of Fluorocarbon Emulsions," Springer, Tokyo, 2005, International Symposia for Life Sciences and Medicine, vol. 12, pp. 237-251.
Chemical Book, 5-Fluorouracil, available at <http://www.chemicalbook.com/ChemicalProductProperty_EN_CB8162744.htm>, accessed Mar. 7, 2014, 1 page.
Deschamps, J. et al., "Solubility of oxygen, carbon dioxide and water in semifluorinated alkanes and in perfluorooctylbromide by molecular simulation", Journal of Fluorine Chemistry, Elsevier, vol. 125, No. 3, 2004.
Elkeeb, R. et al., "Transungual Drug Delivery: Current Status," International Journal of Pharmaceutics, 2010, 384:1-8.
Fischer, K.M., et al., "Effects of a topically applied 2% delta-9-tetrahydrocannabinol ophthalmic solution on intraocular pressure and aqueous humor flow rate in clinically normal dogs," American Journal of Veterinary Research, 2013, 74(2):275-280, Abstract Only (2 pages).
Gerdenitsch, "Emulsions—established and promising drug carriers for parenteral administration," retrieved from Internet, date accessed: Jun. 20, 2016, 2 pages URL: <http://ipimediaworld.com/wp-content/uploads/2012/05/Pages-from-IPI-Volumer-2-Issue-1-11.pdf.>.
Gopal et al., "Use of intravitreal injection of triamcinolone acetonide in the treatment of age-related macular degeneration," Indian J Ophthalmol., 2007, 55(6):431-435, (8 pages).
Griffin, W., "Classification of Surface-Active Agnets by 'HLB'," Journal of The Society of Cosmetic Chemists,1949, 1:311-326.
Grotenhermen, F., "Cannabinoids for therapeutic use—Designing systems to increase efficacy and reliability," American Journal of Drug Delivery, 2004, 2(4):229-240, Abstract Only (19 pages).
Ishizaki et al., "Treatment of Diabetic Retinopathy," Forum: Complication, Practice, 2009, 26(5): 474-476 (3 pages).
Jonas et al., "Intravitreal triamcinolone acetonide for exudative age-related macular degeneration," Br J Ophthalmol, 2003, 87:462-468.
Joussen et al., "The concept of heavy tamponades—chances and limitations," Graefes Arch Exp Ophthalmol, 2008, 246:1217-1224.
Knepp et al., "Stability of Nonaqueous Suspension Formulations of Plasma Derived Factor IX and Recombinant Human Alpha Interferon at Elevated Temperatures," Pharmaceutical Research, 1998, 15 (7):1090-1095.
Martín-Montañez et al., "End-of-day dryness, corneal sensitivity and blink rate in contact lens wearers," Cont Lens Anterior Eye, 2015, 38(3):148-51.
Matteucci et al., "Biocompatibility assessment of liquid artificial vitreous replacements: relevance of in vitro studies," Survey of Ophthalmology, 2007, 52(3):289-299, Abstract Only (1 page).
Murdan, S., "Enhancing the Nail Permeability of Topically Appied Drugs," Expert Opinion on Drug Delivery, 2008, 5 (11):1267-1282.
Pinarci, E. et al., "Intraocular Gas Application in the Diagnosis and Treatment of Valsalva Retiopathy in Case with Premacular Hemorrhage," XP002625604, Retina Vitreus, 2009, 17 (2):153-155, 1 page, abstract only.
Rosca-Casian, O. et al., "Antifungal Activity of *Aloe vera* Leaves," Fitoterapia, 2007, 28, 219-222.
Rosenberg, A., "Effects of Protein Aggregates: An Immunologic Perspective," The AAPS Journal, 2006, 8 (3), E501-E507.
Sato et al., "Vitrectomy and Intraocular Lens Implantation for Cytomegalovirus Retinitis in a Patient with Acquired Immunodeficiency Syndrome," Presented by Medical Online, New Ophthalmology, 1999, 16(7): 995-998 (4 pages).
Stevenson, C., "Characterization of Protein and Peptide Stability and Solubility in Non-Aqueous Solvents," Current Pharmaceutical Biotechnology, 2000, 1, 165-182.
Wang, W., "Lyophilization and Development of Solid Protein Pharmaceuticals," International Journal of Pharmaceutics, 2000, 203, 1-60.
"What is retinal vitrectomy?" Presented by: Medical Online, Obesity and Diabetes Mellitus, 2005, 4(2): 284-286 (3 pages).
Wu et al., "Physicochemical characterization and aerosol dispersion performance of organic solution advanced spray-dried cyclosporine A multifunctional particles for dry powder inhalation aerosol delivery," International Journal of Nanomedicine, 2013, 8:1269-1283.
Xalatan, Latanoprost Ophthalmic Solution, 50 µg/mL Prostaglandin $F_{2\alpha}$ analogue, Product Monograph, Jul. 21, 2014, 30 pages.
Yaoxue Zhuanye Zhishi II (Editor: Jin Xiangqun), Military Medical Science Press, $1^{st}$ Printing of $2^{nd}$ Edition, Mar. 2009, p. 158.
Yaoxue Zhuanye Zhishi II (Editor: Jin Xiangqun), Military Medical Science Press, $1^{st}$ Printing of $2^{nd}$ Edition, Mar. 2009, p. 158, 3 pages (English Machine Translation).

\* cited by examiner

PHARMACEUTICAL COMPOSITIONS COMPRISING SEMIFLUORINATED ALKANES FOR THE TREATMENT OF CONTACT LENSE-RELATED CONDITIONS

CROSS-REFERENCE TO RELATED APPLICATIONS

This application is a U.S. national stage application filed under 35 U.S.C. § 371 of International Application No. PCT/EP2018/062027, filed on May 9, 2018, which claims priority to, and the benefit of, European Application No. 17170826.6, filed on May 12, 2017, the contents of each of which are incorporated herein by reference in their entireties.

FIELD

The present invention is in the field of compositions comprising semifluorinated alkanes for use in the treatment or prevention of ocular diseases.

BACKGROUND OF THE INVENTION

The use of contact lenses becomes more and more popular as an alternative for wearing spectacles for various reasons. In many cases, contact lenses provide for a better correction of the vision as well as functional advantages especially for sports and outdoor activities. Furthermore, contact lenses are preferred over spectacles for aesthetic considerations by many users. Recently, soft contact lenses have become inexpensive and readily available, allowing for higher comfort of use and varying periods of utilization and wear, from as short as one day up to a couple of days. In particular, disposable contact lenses for single use have become standard today.

One of the widespread complications associated with wearing contact lenses, however, is the dryness of the eye during and especially as a result of prolonged wearing of contact lenses. The use of aqueous artificial tears to provide some relief to the sensation of dryness in many cases is insufficient as it does not result in the formation of a stable, long lasting relief of dryness.

WO 2011/073134 A1 discloses pharmaceutical compositions for the treatment of keratoconjunctivitis sicca (dry eye disease) comprising liquid vehicles which include one or more semifluorinated alkanes. The compositions incorporate an active ingredient selected from the of macrolide immunosuppressants and can be administered topically into the eye. Contact lens wearing is described among the risk factors to develop keratoconjunctivitis sicca.

WO2014/041055 A1 refers to compositions comprising at least two or more semifluorinated alkanes. The compositions can be used as medicines that are topically administered to an eye or ophthalmic tissue, such as for use in the treatment of keratoconjunctivitis sicca (dry eye disease) and/or meibomian gland dysfunction and symptoms associated therewith. As non-pharmacological approaches for the treatment of keratoconjunctivitis sicca, the avoidance of exacerbating factors such as dry air, wind and drafts, tobacco smoke, modification of working habits; eye lid hygiene; tear supplementation; physical tear retention by punctal plugs or therapeutic contact lenses are mentioned.

WO 2017/055453 A1 refers to ophthalmic compositions comprising semifluorinated compounds characterized by the general formula $CF_3$—$(CF_2)_n$—$CH(CH_3)$—$(CH_2)_m$—$CH_3$ wherein n is an integer selected from 3 to 5 and m is an integer selected from 1 to 5, as well as the use of the composition as a medicament for topical administration to the eye. Among other studies, the document describes tear film analysis studies in dry eye disease from which patients wearing contact lenses were excluded.

Furthermore, WO 2017/055454 A1 refers to compositions comprising $CF_3(CF_2)_5(CH_2)_7CH_3$ and $CF_3$—$(CF_2)_5$—$CH(CH_3)$—$(CH_2)_5$—$CH_3$ as well as their use as medicaments for topical administration to the eye. In this case, tear film analysis studies from which patients wearing contact lenses were excluded are also described.

WO 2005/123035 A1 discloses hydrophobic ophthalmic compositions adapted for use in a patient's eye or on a contact lens inserted into a patient's eye and having a viscosity of 1 to 15,000 centistokes. The composition includes a silicone polymer, fluorinated silicone polymer, fluorocarbon polymer fluorinated alcohol, or perfluorinated polyether composition, singly or blended, adapted to coat at least a portion of a contact lens inserted in a patient's eye.

Martin-Montanez et. al. (Cont Lens Anterior Eye. 2015; 38(3):148-51) refer to end-of-day dryness (EOD dryness), as a symptom of preferentially soft contact lens wearers with multifactorial etiology with a prevalence of 28-72%, with a substantial number of contact lens wearers showing no clinical signs.

WO 2007/008666 A2 describes a method of improving a patient's vision comprising providing a composition comprising at least one polymer selected from the group consisting of silicones, fluorinated silicones, perfluorocarbons, fluorinated alcohols, and fluorinated polyethers; and applying the composition to at least one surface of a contact lens for insertion into the patient's eye.

Accordingly, for contact lens wearers, especially those wearing contact lenses on a regular and/or prolonged basis, no satisfactory relief for the treatment or prevention of undesirable implications relating to an ocular surface of an eye, such as, for example, discomfort, dryness or pain during or especially after wearing the contact lenses presently is available.

It is therefore an object of the present invention to provide compositions which may avoid some of the disadvantages of the prior art, and which may be useful in the treatment or prevention of diseases or conditions relating to an ocular surface of an eye of an individual, wherein the individual is a contact lens wearer. Further objects of the invention will be clear on the basis of the following description of the invention, examples and claims.

Furthermore, it is an object of the present invention to provide compositions that are suitable to treat, ameliorate, reduce dryness of the eye or diseases or conditions associated therewith as a result of soft contact lens wear.

Further objects of the invention will become clear on the basis of the following description, examples, and patent claims.

SUMMARY OF THE INVENTION

In a first aspect, the present invention provides a pharmaceutical composition comprising a semifluorinated alkane of formula (I)

$$F(CF_2)_n(CH_2)_mH \qquad (I)$$

wherein
n is an integer from 4 to 6, and
m is an integer from 5 to 8, for use in the treatment or prevention of a disease or condition relating to an ocular surface of an eye of an individual, wherein the individual is a contact lens wearer, and wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or wherein the contact lens is a silicone hydrogel contact lens and the composition is administered topically to a surface of the eye of the individual after the contact lens has been removed from the eye of the individual.

More specifically, according to this aspect, the present invention also provides a pharmaceutical composition essentially consisting of 1-perfluorohexyl-octane (F6H8), for use in the treatment or prevention of a disease or condition relating to an ocular surface of an eye of an individual, wherein the individual is a contact lens wearer, and wherein the contact lens is a hydrogel contact lens or a silicone hydrogel contact lens and wherein the composition is administered topically to a surface of the eye of the individual after the contact lens has been removed from the eye of the individual.

In a second aspect, the present invention provides methods for the treatment or prevention of a disease or condition relating to an ocular surface of an eye of an individual, wherein the individual is a contact lens wearer, comprising topical administration of pharmaceutical composition comprising a semifluorinated alkane of formula (I) as defined above to a surface of the eye of the individual, wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or wherein the contact lens is a silicone hydrogel contact lens and the composition is administered topically to a surface of the eye of the individual after the contact lens has been removed from the eye of the individual.

More specifically, according to this aspect, the present invention also provides for methods for the treatment or prevention of a disease or condition relating to an ocular surface of an eye of an individual, wherein the individual is a contact lens wearer, comprising topical administration of pharmaceutical composition essentially consisting of 1-perfluorohexyl-octane (F6H8), for use in the treatment or prevention of a disease or condition relating to an ocular surface of an eye of an individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual.

In a third aspect, the present invention provides for the use of a pharmaceutical composition comprising a semifluorinated alkane of formula (I) as defined above for the preparation of a medicament for the treatment or prevention of a disease or condition relating to an ocular surface of an eye of an individual, wherein the individual is a contact lens wearer, and wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or wherein the contact lens is a silicone hydrogel contact lens and the composition is administered topically to a surface of the eye of the individual after the contact lens has been removed from the eye of the individual.

More specifically, according to this aspect, the present invention also provides for the use of a pharmaceutical composition essentially consisting of 1-perfluorohexyl-octane (F6H8), for the preparation of a medicament for the treatment or prevention of a disease or condition relating to an ocular surface of an eye of an individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual.

In a fourth aspect, the present invention relates to a kit comprising a pharmaceutical composition for use according to the first aspect of the present invention, a container for holding said composition, means for dispensing said composition to the eye of the individual or patient and optionally instructions on how to use and apply said composition when wearing contact lenses.

DETAILED DESCRIPTION OF THE INVENTION

In the first aspect, the present invention provides a pharmaceutical composition comprising a semifluorinated alkane of formula (I)

$$F(CF_2)_n(CH_2)_mH \qquad (I)$$

wherein n is an integer from 4 to 6, and m is an integer from 5 to 8, for use in the treatment or prevention of a disease or condition relating to an ocular surface of an eye of an individual, wherein the individual is a contact lens wearer, and wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or wherein the contact lens is a silicone hydrogel contact lens and the composition is administered topically to a surface of the eye of the individual after the contact lens has been removed from the eye of the individual.

The pharmaceutical compositions for use according to the present invention comprise a semifluorinated alkane (which may also be referred to in abbreviated form as an SFA), which may be defined as a linear compound composed of at least one perfluorinated segment (F-segment) and at least one non-fluorinated hydrocarbon segment (H-segment).

In an alternative nomenclature for the specified semifluorinated alkanes as noted in parentheses below and as may be further used herein, is based on the general formula FnHm, wherein F means the linear perfluorinated hydrocarbon segment, H means the linear non-fluorinated hydrocarbon segment and n, m is the number of carbon atoms of the respective segment. For example, F4H5 may be used to denote 1-perfluorobutyl-pentane or $CF_3(CF_2)_3$—$(CH_3)_4CH_3$ (which may be also, alternatively expressed as formula $F(CF_2)_4(CH_2)_5H$), which has a linear perfluorinated segment F with four carbons (n=4) and a linear non-fluorinated hydrocarbon segment with five carbons (m=5). Furthermore, F6H8 may be used to denote 1-perfluorohexyl-octane or $CF_3(CF_2)_5$—$(CH_3)_7CH_3$ (which may be also, alternatively expressed as formula $F(CF_2)_6(CH_2)_8H$), which has a linear perfluorinated segment F with six carbons (n=6) and a linear non-fluorinated hydrocarbon segment with 8 carbons (m=8).

The pharmaceutical compositions for use according to present invention comprise a semifluorinated alkane of formula (I):

$$F(CF_2)_n(CH_2)_mH \qquad (I)$$

wherein n is independently selected from an integer from 4 to 6, and m is independently selected from an integer from 5 to 8.

Accordingly, said semifluorinated alkane may be selected from $CF_3(CF_2)_3$—$(CH_2)_4CH_3$ (F4H5), $CF_3(CF_2)_3$—$(CH_2)_5CH_3$ (F4H6), $CF_3(CF_2)_3$—$(CH_2)_6CH_3$ (F4H7), $CF_3(CF_2)_3$—$(CH_2)_7CH_3$ (F4H8), $CF_3(CF_2)_4$—$(CH_2)_4CH_3$ (F5H5), $CF_3(CF_2)_4$—$(CH_2)_5CH_3$ (F5H6), $CF_3(CF_2)_4$—$(CH_2)_6CH_3$ (F5H7), $CF_3(CF_2)_4$—$(CH_2)_7CH_3$ (F5H8), $CF_3(CF_2)_5$—$(CH_2)_4CH_3$ (F6H5), $CF_3(CF_2)_5$—$(CH_2)_5CH_3$ (F6H6), $CF_3(CF_2)_5$—$(CH_2)_6CH_3$ (F6H7) and $CF_3(CF_2)_5$—$(CH_2)_7CH_3$ (F6H8). More preferably, said semifluorinated alkane may be selected from $CF_3(CF_2)_3$—$(CH_2)_4CH_3$ (F4H5) and $CF_3(CF_2)_5$—$(CH_2)_7CH_3$ (F6H8).

In a preferred embodiment, the pharmaceutical composition for use according to the present invention comprises a semifluorinated alkane of formula (I) which is selected from 1-perfluorohexyl-octane ($CF_3(CF_2)_5$—$(CH_2)_7CH_3$ (F6H8)) and 1-perfluorobutyl-pentane ($CF_3(CF_2)_3$—$(CH_2)_4CH_3$ (F4H5)).

The pharmaceutical compositions of the invention comprising of "a" semifluorinated alkane is to be understood herein, as comprising at least one semifluorinated alkane of Formula (I) as described above. Optionally, however, the composition may comprise of more than one, for example, a mixture of two or more semifluorinated alkanes of Formula (I), i.e. of any one of the semifluorinated alkane species as described above.

In yet further embodiment, the pharmaceutical composition of the present invention may consist of a semifluorinated alkane of Formula (I) as specified above. In this context, the term "a" semifluorinated alkane is to be understood as at least one semifluorinated alkane, but may also include the option of more than one, or a plurality of semifluorinated alkane compounds. Accordingly, in one embodiment, the composition may consist of more than one semifluorinated alkane of Formula (I) as specified above.

As used herein, the term "consists" and related terms "consisting" or "consist" is to be understood as meaning that no other features, other than those prefaced by the term are present. In the context of compositions, if any other constituent or component is present in the composition other than those prefaced by such term, then it is present only in trace or residual amounts such as to confer no technical advantage or relevance in respect of the object of the invention, such as may be further understood by the term 'essentially" or "substantially" used in conjunction with these terms (e.g. 'essentially consisting of'). In contrast, the term 'comprising" or related terms "comprises" or "comprise" in the context of the present compositions, is to be understood as meaning that other features, other than those prefaced by the term may be present in the composition.

In yet a further embodiment, the pharmaceutical composition for use according to the present invention as defined in any of the previous embodiments described above, preferably comprises a semifluorinated alkane or optionally, a mixture of semifluorinated alkanes in an amount of at least 70% (w/w), 75% (w/w), 85% (w/w), 90% (w/w), 95% (w/w), 98% (w/w), 98.5% (w/w), 99% (w/w), 99.5% (w/w), 99.8% (w/w) or at least 99.9% (w/w) of a semifluorinated alkane or a mixture of semifluorinated alkanes as described above, with respect to the total weight of the composition. In one preferred embodiment, the composition of the present invention is 100% (w/w) of a semifluorinated alkane or mixture of semifluorinated alkanes.

The term "% (w/w)" as used herein and unless indicated otherwise refers to the amount of a component of a composition as a weight percentage in relation to the total weight of the composition (with 'w' denoting weight). For instance, the pharmaceutical composition according to the present invention may comprise up to about 1.5% (w/w) of a co-solvent such as ethanol, relative to the total weight of the composition.

In a particularly preferred embodiment, the pharmaceutical composition for use according to the present invention comprises 1-perfluorohexyl-octane ($CF_3(CF_2)_5$—$(CH_2)_7CH_3$ (F6H8)), preferably as the only semifluorinated alkane present in the pharmaceutical composition. In a further preferred embodiment, the pharmaceutical composition of the present invention essentially consists of 1-perfluorohexyl-octane (F6H8). With regard to this preferred embodiment, the term "the pharmaceutical composition essentially consisting of 1-perfluorohexyl-octane (F6H8)" may be understood as a pharmaceutical composition which has 1-perfluorohexyl-octane (F6H8) as the major constituent in an amount of at least 98% (w/w), 98.5% (w/w), 99% (w/w), 99.5% (w/w), 99.8% (w/w) or at least 99.9% (w/w) with regard to the total weight of the final composition, whereas only minor components or impurities such as isomers of F6H8 or unavoidable side-products from the manufacture of F6H8 and/or residual moisture might be present in an amount of up to 2% (w/w) or of up to 1.5% (w/w) or of up to 1% (w/w) or of up to 0.5% (w/w) or of up to 0.2% (w/w) or of up to 0.1% (w/w) with regard to the final composition.

In yet a further preferred embodiment, the compositions for use according to the present invention may be substantially free of water. In further embodiment, the compositions for use according to the invention may be substantially free of a preservative. In an optional embodiment, said compositions may however include a further active ingredient and/or one or more excipients.

The preferred semifluorinated alkane, F4H5, also known as 1-perfluorobutyl-pentane, and which has the chemical formula $F(CF_2)_4(CH_2)_5H$ is a chemically and physiologically inert, water-insoluble liquid, with a density of 1.284 g/cm$^3$ at 25° C. and refractive index of 1.3204 at 20° C. The particularly preferred semifluorinated alkane, F6H8, also known as 1-perfluorohexyl-octane, is also a chemically and physiologically inert, water-insoluble liquid, and has a density of 1.35 g/cm$^3$ at 25° C. and refractive index of 1.3432 at 20° C.

The pharmaceutical composition according to the present invention are useful for the treatment, therapy, amelioration or prevention of a disease or condition or any symptoms relating to an ocular surface of an eye of an individual, wherein the individual is a contact lens wearer. The term "condition" as used herein, more specifically relates to a pathological condition that may be treated by the use of the compositions of the present invention.

As understood herein, the use of a composition of the present invention in the context of prevention of a disease or condition, or in a prophylactic treatment refers to use of said composition so as to prevent occurrence, or exacerbation, or risk of occurrence (or re-occurrence) of said disease or condition in an individual.

The term "contact lens wearer" as used herein means a person, individual or patient wearing contact lenses, i.e. an individual wearing contact lenses or a contact lens inserted to an eye or to both of its eyes. Preferably, the term "contact lens wearer" depicts a person or individual wearing contact lenses on a more than occasional basis, or rather regularly. For example, the term "contact lens wearer" according to the present invention comprises individuals wearing a contact lens or contact lenses at least once every 2 weeks, preferably at least once every 7 days, or at least once every 6 days, every 5 days, every 4 days, every 3 days or at least once every 2 days. Preferably, the term "contact lens wearer" depicts an individual wearing contact lenses every day or on 6 days, 5 days, 4 days, 3 days or 2 days out of 7 days.

Furthermore, the term "contact lens wearer" as used herein comprises individuals wearing contact lenses that may inserted to the eye or eyes of the individual for different periods of time, depending on the particular kind of contact lens, such as, for example from an hour or several hours, for example from one to 24 hours, up to several days, such as 2, 3, 4, 5 or 7 days or even one week to several weeks.

In one embodiment of the present invention, the contact lens is a hydrogel contact lens and the composition is administered topically to a surface of the eye of the individual before the contact lens is inserted to the eye of the individual and/or during contact lens wear and/or after the contact lens has been removed from the eye of the individual.

The term "hydrogel contact lens" as used herein means a hydrogel contact lens that does not comprise substantial amounts of silicone containing constituents, for example, that does not comprise more than about 5% (w/w), preferably not more than about 3% (w/w) and even more preferably not more than about 1% (w/w) of silicone containing constituents such as, for example silicone, silicone acrylate, t-butylstyrene silicone acrylate and/or fluoro silicone acrylate. Preferably, a "hydrogel contact lens" according to the present invention does not comprise any silicone containing constituents and may also be referred to as a non-silicone hydrogel. The hydrogel contact lenses according to the present invention preferably belong to a class of soft hydrophilic plastic contact lenses, which may be categorized according to the US Food and Drug Administration (FDA) by their plastic composition and water content into 4 groups, including:

Group 1: Non-ionic plastic material with a water content <50%;

Group 2: Non-ionic plastic material with a water content ≥50%;

Group 3: Ionic plastic material with a water content <50%; and

Group 4: Ionic plastic material with a water content ≥50%.

For example, the hydrogel contact lens or hydrogel contact lenses relevant in the context of the present invention may comprise or may be fabricated from a hydrophilic plastic material selected from the of the group consisting of: Acofilcon A; acofilcon B; alphafilcon A; altraficon A; bufilcon A; crofilcon; deltafilcon A; dimefilcon A; droxifilcon A; epsifilcon A; etafilcon A; focofilcon A; hefilcon A & B; hefilcon C; hilafilcon B; hioxifilcon A; hioxifilcon B; hioxifilcon D; isofilcon; lidofilcon A; lidofilcon B; mafilcon; methafilcon A, B; nelfilcon A; nescofilcon A; netrafilcon A; ocufilcon A; ocufilcon B; ocufilcon C; ocufilcon D; ocufilcon E; ocufilcon F; ofilcon A; omafilcon A; perfilcon A; phemfilcon A; phenfilcon A; polymacon; scafilcon A; surfilcon A; tefilcon; tetrafilcon A; tetrafilcon B; vasurfilcon A; vifilcon A; and xylofilcon A.

Contact lenses according to Group 1 as defined above may, for example, comprise or be fabricated from a plastic material selected from the group consisting of: Acofilcon B (49%); crofilcon (39%); dimefilcon A (36%); hefilcon A & B (45%); hioxifilcon B (49%); isofilcon (36%); mafilcon (33%); polymacon (38%); tefilcon (38%) and tetrafilcon A (43%) (with water content given in brackets).

Contact lenses according to Group 2 as defined above may, for example, comprise or be fabricated from a plastic material selected from the group consisting of: Acofilcon A (58%), alphafilcon A (66%), altraficon A (65%), hefilcon C (57%), hilafilcon B (59%), hioxifilcon A (59%), hioxifilcon D (54%), lidofilcon B (79%), lidofilcon A (70%), nelfilcon A (69%), nescofilcon A (78%), netrafilcon A (65%), ofilcon A (74%), omafilcon A (59%), scafilcon A (71%), surfilcon A (74%), vasurfilcon A (74%) and xylofilcon A (67%) (with water content given in brackets).

Contact lenses according to Group 3 as defined above may, for example, comprise or be fabricated from a plastic material selected from the group consisting of: Bufilcon A (45%), deltafilcon A (43%), droxifilcon A (47%), ocufilcon A (44%), phenfilcon A (38%) (with water content given in brackets).

Contact lenses according to Group 4 as defined above may, for example, comprise or be fabricated from a plastic material selected from the group consisting of: Bufilcon A (55%), epsifilcon A (60%), etafilcon A (58%), focofilcon A (55%), methafilcon A, B (55%), ocufilcon B (53%), ocufilcon C (55%), ocufilcon D (55%), ocufilcon E (65%), ocufilcon F (60%), perfilcon A (71%), phemfilcon A (55%), tetrafilcon B (58%), vifilcon A (55%) (with water content given in brackets).

Exemplary hydrogel contact lenses that may be worn by the contact lens wearing individual according to the present invention comprise SofLens® 38 as a hydrogel contact lens fabricated from hydrophilic plastic material referred to as polymacon, which is co-polymer of 2-Hydroxyethylmethacrylate (2-HEMA), cross-linked with ethylene glycol dimethacrylate (EGDMA); further soft hydrophobic plastic contact lenses fabricated from polymacon include SofLens® Natural Colors.

In an alternative embodiment of the present invention, the contact lens is a silicone hydrogel contact lens and the composition is administered topically to a surface of the eye of the individual after the contact lens has been removed from the eye of the individual.

The silicone hydrogel contact lenses according to the present invention preferably belong to Groups II or III of the class of the hydrophobic plastic contact lenses as defined by the US Food and Drug Administration (FDA). The silicone hydrogel contact lenses relevant in this context of the present invention may comprise or may be fabricated from a plastic silicone material, namely comprising silicone, silicone acrylate, t-butylstyrene silicone acrylate and/or fluoro silicone acrylate. Exemplary silicone hydrogel contact lenses according to the present invention may comprise or may be fabricated from plastic material selected from the group consisting of: Balafilcon A (36%), comfilcon A (48%), efrofilcon A (74%), enfilcon (46%), galyfilcon A (47%), lotrafilcon A (24%), lotrafilcon B (33%), narafilcon B (48%), senofilcon A (37%), somofilcon A (56%) and sifilcon A (32%) (with water content given in brackets).

Exemplary silicone hydrogel contact lenses that may be worn by the contact lens wearing individual according to the present invention comprise Clariti® 1 day as a silicone hydrogel contact lens fabricated from a hydrophobic plastic material referred to as Somofilcon A (FDA, hydrophobic plastic contact lenses group II; 56% water content), which is hydrophilic co-polymer of silicone containing monomers and hydrophilic monomers which is cross-linked with tetraethyleneglycol dimethacrylate including a benzophenone UV absorbing monomer.

In a preferred embodiment, the hydrogel or silicone hydrogel contact lenses worn by the contact lens wearer of the present invention is a disposable soft contact lens, more specifically a disposable soft contact lens for single use. In a further preferred embodiment, the hydrogel or silicone hydrogel contact lenses worn by the contact lens wearer of the present invention is a is a daily wear or extended wear contact lens.

Furthermore, the contact lens worn by the contact lens wearer of the present invention may be a corrective contact lens and/or a therapeutic contact lens and/or a cosmetic or decorative contact lens. Preferably, however, the contact lens may be a corrective contact lens and/or a cosmetic or decorative contact lens. In further embodiments, the contact lens worn by the contact lens wearer according to the present invention is not a therapeutic contact lens. In other embodiments, the contact lens is a corrective contact lens to correct defective vision of the contact lens wearer. In yet further embodiments, the contact lens is a cosmetic or decorative contact lens that change the appearance of the eye of the contact lens wearer.

According to the present invention, the pharmaceutical composition comprising a semifluorinated alkane is administered topically to a surface of the eye of the individual independent of whether the contact lens is a hydrogel contact lens or a silicone hydrogel contact lens. In preferred embodiments, the pharmaceutical composition may be administered dropwise to a surface of the eye of the contact lens wearer, preferably by dropwise instillation of the pharmaceutical composition to a surface of the eye of the contact lens wearer. The term "surface of the eye" is to be understood to comprise all surfaces of the eye or parts thereof that can be accessed for instillation. In a broad sense the term "surface of the eye" may also comprise surface areas of the eye that are covered by a contact lens already inserted before the administration of the pharmaceutical composition, more specifically by an inserted hydrogel contact lens.

Furthermore, the term "surface of the eye" as used herein may comprise surface areas of the eye and any such region or tissue of the eye that may be accessible to topical administration, such as to the cornea or conjunctiva, or the eyelid margins or corners, the lower eyelid and/or the eye sac of an eye of a contact lens wearer. In a preferred embodiment, the pharmaceutical composition for use according to the present invention is administered by dropwise instillation to the surface of the eye, to the lower eye lid or into the eye sac of the eye of the individual or patient.

In the first alternative embodiment of the pharmaceutical composition for use according to the present invention, the contact lens is a hydrogel contact lens or more specifically a non-silicone, or a silicone-free hydrogel contact lens. In this alternative embodiment, the composition is administered topically to the surface of the eye of the individual before the contact lens is inserted to the eye of the individual and/or during contact lens wear and/or after the contact lens is has been removed from the eye of the individual. In one embodiment, the pharmaceutical composition is administered topically to the surface of the eye of the individual before the contact lens is inserted in the eye of the individual. In cases in which the composition is administered topically to the surface of the eye of the individual or patient before the contact lens is inserted to the eye of the individual the pharmaceutical composition is administered to the surface of the eye by the individual itself or any other person without the hydrogel contact lens being inserted or present in the eye. It should be understood, however, that the hydrogel contact lens as described above may then be inserted a period of time after the pharmaceutical composition has been administered to the eye, for example about 1 hour to 2 hours or as short as about 10 min to about 1 minute or even shorter after the pharmaceutical composition has been administered.

Furthermore, according to this embodiment, as long as the contact lens is a hydrogel contact lens, or more specifically a non-silicone, or a silicone-free hydrogel contact lens, the pharmaceutical composition for use according to the present invention can be administered to the surface of the eye after the contact lens has been inserted to the eye and before the contact lens has been removed from the eye. In this embodiment, the pharmaceutical composition may be administered topically to the surface of the eye of the individual during contact lens wear. The pharmaceutical composition may then be administered to the surface of the eye to an area which may or may not be covered by the inserted contact lens.

It should be noted, however that the pharmaceutical composition can be administered to the eye of the contact lens wearer repeatedly, as described in further detail below. In one embodiment, the pharmaceutical composition can be administered before insertion of the hydrogel contact lens and be continued or repeated during hydrogel contact lens wear. In a preferred embodiment of this aspect of the present invention, the pharmaceutical composition for use according to the present invention and the hydrogel contact lens are simultaneously present in the eye of the individual.

In another embodiment in which the contact lens is a hydrogel contact lens, i.e. a non-silicone hydrogel contact lens as defined above, the pharmaceutical composition for use according to the present invention may also be administered to the surface of the eye of a contact lens wearer after the contact lens is has been removed from the eye of the individual. Again, it should be noted that the administration of the composition to the surface of the eye may be carried out after a period of time following the removal of the hydrogel contact lens ranging from seconds to several hours. Furthermore, the administration can be carried out one single time or repeated times after the contact lens has been removed, as outlined further below.

In the second alternative embodiment of the pharmaceutical composition for use according to the present invention, the contact lens is a silicone hydrogel contact lens as described above. In this alternative embodiment, the composition is administered topically to the surface of the eye of the individual exclusively after the contact lens is has been removed from the eye of the individual. It should be noted, that in this second alternative of the present invention directed to silicone hydrogel contact lenses the pharmaceutical composition for use according to the present invention comprising a semifluorinated alkane and the contact lens, more specifically the silicone hydrogel contact lens as defined above, are not simultaneously present in the eye of the individual.

In this case, as long as the silicone hydrogel contact lens has been removed from the eye of the contact lens wearer the administration can also be carried out one single time or repeated times after the contact lens has been removed, as outlined further below.

It should be noted that for either one or both of the alternative embodiments, namely the embodiment related to hydrogel contact lenses as well as for the embodiment related to silicon hydrogel contact lenses, it is possible that the composition is administered topically to the surface of the eye of the individual after the contact lens is has been removed from the eye of the contact lens wearer. This is especially beneficial for the regeneration of the eye or the ocular surface, respectively, overnight after removal of the hydrogel or silicone hydrogel contact lens. Preferably, this is especially beneficial for the treatment, relief or the amelioration of EOD dryness.

Accordingly, in a specific embodiment, the present invention provides a pharmaceutical composition essentially consisting of 1-perfluorohexyl-octane (F6H8), for use in the treatment or prevention of a disease or condition relating to an ocular surface of an eye of an individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual.

According to this specific embodiment, the compositions for use according to the present invention essentially consists of or consists of 1-perfluorohexyl-octane (F6H8) as described above. In this specific embodiment, the contact lens may be either a hydrogel contact lens as described above or a silicone hydrogel contact lens as described above, preferably, however, a hydrogel contact lens. Furthermore, in this specific embodiment, the composition for use according to the present invention is also administered topically to the surface to the eye of the contact lens wearer as described in connection with the more general embodiments of the present invention. According to this specific embodiment, however, the composition for use according to the present invention is administered topically to a surface of the eye of the individual after the contact lens has been removed from the eye of the individual.

In connection with this specific embodiment also, it should be noted that the administration of the composition to the surface of the eye may be carried out after a period of time following the removal of the hydrogel or silicone hydrogel contact lens ranging from seconds to several hours, such as from about 1 or 2 seconds up to 1 or 2 hours, or from about 5 sec up to 1 hour or 45 or 30 min, or from about 1 min up to about 15 or 20 min. Furthermore, the administration can be carried out one single time or repeated times after the contact lens has been removed, as outlined further below.

In further embodiments, the administration of the composition for use according to the present invention to the surface of the eye may be carried out a period of time before the same or another hydrogel or silicone hydrogel contact lens is inserted into the eye again. In specific embodiments, the composition for use according to the present invention is administered at least 0.5 to 10 hours, more preferably 1 to 10 hours, most preferably 2 to 8 hours before the same or another hydrogel or silicone hydrogel contact lens is inserted into the eye again. Accordingly, in these embodiments the last administration of the composition for use according to the present invention is carried out at least 0.5 to 10 hours, more preferably 1 to 10 hours, most preferably 2 to 8 hours before the same or another hydrogel or silicone hydrogel contact lens is inserted into the eye again.

In further specific embodiments, the composition for use according to the present invention is administered at least 2 to 10 hours, more preferably 4 to 10 hours, most preferably 6 to 10 hours before the same or another silicone hydrogel contact lens is inserted into the eye again. Accordingly, in these embodiments the last administration of the composition for use according to the present invention is carried out at least 2 to 10 hours, more preferably 4 to 10 hours, most preferably 6 to 10 hours before the same or another silicone hydrogel contact lens is inserted into the eye again.

In yet further specific embodiments, the composition for use according to the present invention is administered at least 0.5 to 10 hours, more preferably 1 to 10 hours, most preferably 2 to 10 hours before the same or another hydrogel contact lens is inserted into the eye again. Accordingly, in these embodiments the last administration of the composition for use according to the present invention is carried out at least 0.5 to 10 hours, more preferably 1 to 10 hours, most preferable 2 to 10 hours before the same or another hydrogel contact lens is inserted into the eye again.

It should be noted that in this specific embodiment also, the composition is administered topically to the surface of the eye of the individual exclusively after the contact lens is has been removed from the eye of the individual and that, accordingly, the hydrogel contact lens or the silicone hydrogel contact lens as defined above, are not simultaneously present in the eye of the individual. In this case also, as long as the hydrogel or silicone hydrogel contact lens has been removed from the eye of the contact lens wearer the administration can also be carried out one single time or repeated times after the contact lens has been removed, as outlined further below.

As already stated above, the compositions of the present invention comprising a semifluorinated alkane or, in specific embodiments, essentially consisting of the preferred semifluorinated alkane 1-perfluorohexyl-octane (F6H8) are useful in the treatment or prevention of a disease or condition relating to an ocular surface of an eye of an individual, wherein the individual is a contact lens wearer. The term "disease or condition relating to an ocular surface of an eye" may be understood to comprise any disease or condition, more specifically pathological condition, that is associated with, or caused by dryness or a lack or an insufficient supply or replenishment of tear fluid to the ocular surface of the eye of a contact lens wearer.

Typical symptoms associate therewith comprise discomfort, dryness or pain during or after wearing the contact lenses. Accordingly, in one embodiment, the disease or condition related to the ocular surface of an eye of the individual according to the present invention is discomfort, dryness or pain during or after wearing the contact lenses. Furthermore, the disease or condition related to the ocular surface of an eye of the individual according to the present invention preferably is associated with or at least partly caused by contact lens wear, especially be prolonged or repeated contact lens wear. It should be noted, however, that the "disease or condition relating to an ocular surface of an eye" of the contact lens wearer according to the present invention does not necessarily have to be caused by contact lens wear but may also have different causes such as described in further detail below.

In a preferred embodiment, the disease or condition related to the ocular surface of an eye of the individual according to the present invention is dryness associated with continued, prolonged, repeated and/or regular contact lens wear as described in further detail above. Accordingly, in a preferred embodiment of the present invention, the disease or condition related to the ocular surface of an eye of the individual is dryness associated with continued contact lens wear.

In a further preferred embodiment, the disease or condition related to the ocular surface of an eye of the individual according to the present invention is a pathological condition characterized by the symptom of sensation of dryness in the eye as a result of contact lens wear. This symptom, hereinafter referred to as "EOD dryness" is often also referred to as "end of day dryness or "end-of-day contact lens discomfort", or "delayed subjective dryness", or "contact lens-related discomfort". In yet a further preferred embodiment, the disease or condition related to the ocular surface of an eye of the individual is EOD dryness, preferably contact lens related EOD dryness.

As used herein, EOD dryness relates to a common and clinically well described complication resulting from wearing soft contact lenses. It is characterized by a feeling or sensation of dryness in the eye during lens wear, especially after prolonged periods of time, but also after prolonged wear of soft contact lenses. This common side effect of continued contact lens wear is generally progressive in nature and results in reduced wearing time and, eventually, in discontinuation of contact lens wear. Although contact lenses are stable and properly fitted, in many cases patients complain that the feeling of dryness gets worse with time, especially during the afternoon and evening, with the desire to immediately or urgently remove the lenses. With prevalence rates of up to 77% and EOD dryness being the mayor reason for lens wear discontinuation, it appears worthwhile to develop strategies to treat or ameliorate symptoms of EOD dryness. A substantial number of contact lens wearers suffering from EOD dryness show no clinical signs, however, suffer from the symptoms associated with EOD. Accordingly, individuals or patients suffering from EOD dryness may or may not show signs as abnormal tear film, reduced tear film break-up time, abnormal meibomian secretions and ocular surface damage. Thus, it should be noted that that EOD dryness and dry eye disease (DED) are two different and unrelated clinical entities, with eventually some patients suffering from both EOD dryness and DED as, for example, also described by Martin-Montanez et. al. (Cont Lens Anterior Eye. 2015; 38(3):148-51).

Most importantly, however, it should be pointed out that EOD dryness is a non-chronic, acute syndrome that often occurs during soft contact lens wear and typically intensifies with prolonged wearing periods, especially towards the end of the day. Accordingly, the pharmaceutical composition for use according to the present invention is useful for the treatment amelioration or prevention of a disease or condition, more specifically of EOD dryness or contact lens related EOD dryness which may be characterized by dryness that increases from insertion to removal of the contact lens.

Under normal circumstances, the surface of the eye of the contact lens wearer recovers before the next wearing period. However, it has been proven advantageous to shorten and intensify this recovery period to reduce the sensation of discomfort and eye irritation as much as possible. To reduce the sensation of discomfort and eye irritation effectively, the recovery period after administration of the composition after contact lens wear preferably is at least 1 hour or at least 2 hours. In specific embodiments, the recovery period after administration of the composition for use according to the present invention is from 1 to 10 hours, preferably from 2 to 10 hours, most preferably from 4 to 10 hours. As a result, the tendency to discontinue contact lens wear due to discomfort associated with prolonged contact lens wear may be reduced effectively. Therefore, treatment of a disease or condition related to the ocular surface of an eye such as dryness associated with contact lens wear, in particular dryness associated with prolonged contact lens wear or EOD dryness by topically administering a composition essentially consisting of 1-perfluorohexyl-octane is effective in reducing discomfort associated with contact lens wear. Further, treatment of a disease or condition related to the ocular surface of an eye such as dryness associated with contact lens wear, in particular dryness associated with prolonged contact lens wear or EOD dryness by topically administering a composition essentially consisting of 1-perfluorohexyl-octane is effective in ameliorating and/or reducing dryness or the sensation of dryness after, before and during contact lens wear.

In contrast to dry eye disease (DED) as described below, EOD dryness is a clinical condition that increases over the whole period of contact lens wear, namely starting with low symptoms upon insertion of the contact lens to the eye and increasing with prolonged duration of contact lens wear such as during normal contact lens wear over periods of for example 2 hours or longer, or 3 hours or longer, or 6 hours or longer or even 8 or 10 or even 12 hours or longer during one day until removal of the contact lens from the eye in the afternoon or evening.

Keratoconjunctivitis sicca (dry eye disease, DED) as used herein, in contrast to EOD as described above, is a chronic, bilateral desiccation of the conjunctiva and cornea due to an inadequate tear film. Symptoms may include itching, burning, irritation, and photophobia. Signs of DED often include reduced tear production, reduced tear film break-up time (TBUT), ocular surface damage which can be assessed by means of testing (i.e. Schirmer test, tear breakup test, corneal/conjunctival staining).

Meibomian gland dysfunction (MGD) is considered one of the mayor root causes of DED. MGD is often characterized by meibomian gland obstruction and clogging of the gland through hyperkeratinisation and an increased viscosity of the meibum. Resulting to decreased secretion of meibum affecting the tear film's stability, ultimately giving rise to keratoconjunctivitis sicca (dry eye disease, DED).

In yet a further embodiment, the disease or condition related to the ocular surface of an eye of the contact lens wearer according to the present invention is selected from keratoconjunctivitis sicca (dry eye disease, DED) and/or meibomian gland dysfunction (MGD) and/or symptoms associated therewith. Both keratoconjunctivitis sicca (DED) and meibomian gland dysfunction (MGD) as well as possible symptoms associated therewith can occur together with the diseases or conditions related to the ocular surface of an eye of a contact lens wearer as described above.

Accordingly, in a preferred embodiment of the present invention the contact lens wearer suffers concomitantly from keratoconjunctivitis sicca (DED) and/or meibomian gland dysfunction (MGD) and/or symptoms associated therewith and from a disease or condition related to EOD dryness.

The pharmaceutical compositions for use according to the present invention can be administered topically to the surface of the eye of an individual, i.e. a contact lens wearer as described above, by dropwise administration or instillation or application of drops of the composition to a part of the surface of the eye accessible for topical administration. The ocular surface of the eye may comprise but is not necessary limited to the cornea and/or the conjunctiva and/or the eye lid or any combinations thereof.

Furthermore, the pharmaceutical composition for use according to the present invention can be administered following different administration schemes. For example, the topical administration can be done once a day, typically during contact lens wear (in case the contact lens is a hydrogel contact lens) or preferably, especially in connection with the specific embodiment in which the composition essentially consists of 1-perfluorohexyl-octane (F6H8), after removal of the of the contact lenses, such as in the evening after the contact lenses have been worn for a prolonged period of time during the day. Preferably, however, the dropwise administration of the pharmaceutical composition according to the present invention can be repeated for at least one, two, three, four or five times per day. In each instance of topical administration of the compositions according to the present invention, an amount of about 1 to about 5 drops, preferably 1 to about 3 drops, and most preferably 1 or 2 drops or most preferred just 1 drop of the pharmaceutical composition may be administered to each eye of the contact lens wearer, preferably to each eye in which a contact lens has been or, in the broader aspects, is or will be inserted.

In a second aspect, the present invention relates to a method for the treatment or prevention of a disease or condition relating to an ocular surface of an eye of an individual, wherein the individual is a contact lens wearer, comprising topical administration of pharmaceutical composition comprising a semifluorinated alkane of formula (I)

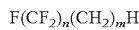  (I)

wherein
n is an integer from 4 to 6, and
m is an integer from 5 to 8,
to a surface of the eye of the individual,
wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or
wherein the contact lens is a silicone hydrogel contact lens and the composition is administered topically to a surface of the eye of the individual after the contact lens has been removed from the eye of the individual.

The method according to this aspect of the invention may or may not comprise steps selected from:
Topical administration of the pharmaceutical composition of the present invention to the surface of the eye of the contact lens wearer;
Insertion of the contact lens to the eye of the contact lens wearer;
Wearing the contact lens;
Removal of the contact lens from the eye of the contact lens wearer;
Repeated topical administration of the pharmaceutical composition of the present invention to the surface of the eye of the contact lens wearer;
Reinsertion of the contact lens to the eye of the contact lens wearer after removal of the contact lens, optionally followed by a waiting period.

Depending on whether the contact lens used in the method according to this aspect of the invention is a hydrogel or a silicone hydrogel contact lens as defined above the named method may be combined in different orders and may be may or may be conducted a single time or repeatedly. In an exemplary embodiment, in case the contact lens is a hydrogel contact lens the method according to this aspect of the invention may comprise the steps of:

a1) Topical administration of the pharmaceutical composition of the present invention to the surface of the eye of the contact lens wearer;
b1) Insertion of the contact lens to the eye of the contact lens wearer;
c1) Wearing the contact lens;
d1) optionally repeated topical administration of the pharmaceutical composition of the present invention to the surface of the eye of the contact lens wearer;
e1) Removal of the contact lens from the eye of the contact lens wearer; and/or
f1) optionally repeated topical administration of the pharmaceutical composition of the present invention to the surface of the eye of the contact lens wearer.

In another exemplary embodiment, in case the contact lens is a silicone hydrogel contact lens the method according to this aspect of the invention may comprise the steps of:

a2) Insertion of the contact lens to the eye of the contact lens wearer;
b2) Wearing the contact lens;
c2) Removal of the contact lens from the eye of the contact lens wearer; and/or
d2) Topical administration of the pharmaceutical composition of the present invention to the surface of the eye of the contact lens wearer;
e2) optionally repeated topical administration of the pharmaceutical composition of the present invention to the surface of the eye of the contact lens wearer.

It should be noted, however, that the method steps as described above may be combined and optionally repeated as appropriate according to the embodiments and preferred embodiments described in detail above for the first aspect of the present invention.

Accordingly, in connection with the specific embodiment of the present invention related to the pharmaceutical compositions essentially consisting of 1-perfluorohexyl-octane (F6H8), for use in the treatment or prevention of a disease or condition relating to an ocular surface of an eye of an individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual the method according to this aspect of the present invention may comprise the steps of:

a3) Insertion of the hydrogel or silicone hydrogel contact lens to the eye of the contact lens wearer;
b3) Wearing the contact lens;
c3) Removal of the contact lens from the eye of the contact lens wearer;
d3) Topical administration of the pharmaceutical composition of the present invention to the surface of the eye of the contact lens wearer; and
e3) optionally repeated topical administration of the pharmaceutical composition of the present invention to the surface of the eye of the contact lens wearer.

Furthermore, the present invention relates to a method for the regeneration of the eye and/or the ocular surface overnight after removal of a contact lens of an eye of an individual, wherein the individual is a contact lens wearer, comprising topical administration of pharmaceutical composition comprising a semifluorinated alkane of formula (I) as described above for the first aspect of the invention, or, according to a specific embodiment essentially consisting of 1-perfluorohexyl-octane (F6H8).

In a third aspect, the present invention relates the use of a pharmaceutical composition comprising a semifluorinated alkane of formula (I)

$$F(CF_2)_n(CH_2)_mH \quad (I)$$

wherein
n is an integer from 4 to 6, and
m is an integer from 5 to 8,
for the preparation of a medicament for the treatment or prevention of a disease or condition relating to an ocular surface of an eye of an individual, wherein the individual is a contact lens wearer, and
wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or
wherein the contact lens is a silicone hydrogel contact lens and the composition is administered topically to a surface of the eye of the individual after the contact lens has been removed from the eye of the individual.

More specifically, according to this aspect, the present invention also provides for the use of a pharmaceutical composition essentially consisting of 1-perfluorohexyl-octane (F6H8), above for the preparation of a medicament for the treatment or prevention of a disease or condition relating to an ocular surface of an eye of an individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual.

In a fourth aspect, the present invention relates to a kit comprising
a pharmaceutical composition for use according to the first aspect of the present invention,
a container for holding said composition,
means for dispensing said composition to the eye of the individual or patient; and optionally
instructions on how to use and apply said composition when wearing contact lenses.

In other words, according to this aspect, the invention relates to a kit for use in the treatment or prevention of a disease or condition relating to an ocular surface of an eye of an individual, comprising
a pharmaceutical composition or pharmaceutical composition for use according to the first aspect of the present invention,
a container for holding said composition,
means for dispensing said composition to the eye of the individual or patient; and optionally
instructions on how to use and apply said composition when wearing contact lenses.

It should be noted, that all embodiments as described above in connection with the first aspect of the invention may also form embodiments or preferred embodiments of the further aspects of the present invention.

The following is a list of numbered items or embodiments of the present invention:

1. A pharmaceutical composition comprising a semifluorinated alkane of formula (I)

$$F(CF_2)_n(CH_2)_mH \quad (I)$$

wherein
n is an integer from 4 to 6, and
m is an integer from 5 to 8, for use in the treatment or prevention of a disease or condition relating to an ocular surface of an eye of an individual, wherein the individual is a contact lens wearer, and
wherein the contact lens is a hydrogel contact lens and the composition is administered topically to a surface of the eye of the individual before the contact lens is inserted to the eye of the individual and/or during contact lens wear and/or after the contact lens has been removed from the eye of the individual, or
wherein the contact lens is a silicone hydrogel contact lens and the composition is administered topically to a surface of the eye of the individual after the contact lens has been removed from the eye of the individual.

2. The pharmaceutical composition for use according to item 1, wherein the semifluorinated alkane of formula (I) is selected from 1-perfluorohexyl-octane (F6H8) and 1-perfluorobutyl-pentane (F4H5).

3. The pharmaceutical composition for use according to item 1 or 2, wherein the composition essentially consists of 1-perfluorohexyl-octane (F6H8).

4. The pharmaceutical composition for use according to any of items 1 to 3, wherein the hydrogel contact lens comprises a plastic material selected from the of the group consisting of: Acofilcon A; acofilcon B; alphafilcon A; altrafilcon A; bufilcon A; crofilcon; deltafilcon A; dimefilcon A; droxifilcon A; epsilfilcon A; etafilcon A; focofilcon A; hefilcon A & B; hefilcon C; hilafilcon B; hioxifilcon A; hioxifilcon B; hioxifilcon D; isofilcon; lidofilcon A; lidofilcon B; mafilcon; methafilcon A, B; nelfilcon A; nescofilcon A; netrafilcon A; ocufilcon A; ocufilcon B; ocufilcon C; ocufilcon D; ocufilcon E; ocufilcon F; ofilcon A; omafilcon A; perfilcon A; phemfilcon A; phenfilcon A; polymacon; scafilcon A; surfilcon A; tefilcon; tetrafilcon A; tetrafilcon B; vasurfilcon A; vifilcon A; and xylofilcon A.

5. The pharmaceutical composition for use according to any of items 1 to 4, wherein the contact lens is a hydrogel contact lens and the composition is administered topically to the surface of the eye of the individual before the contact lens is inserted to the eye of the individual and/or during contact lens wear and/or after the contact lens is has been removed from the eye of the individual.

6. The pharmaceutical composition for use according to item 5, wherein the composition and the contact lens are simultaneously present in the eye of the individual.

7. The pharmaceutical composition for use according to any of items 1 to 5, wherein the composition is administered topically to the surface of the eye of the individual before the contact lens is inserted in the eye of the individual.

8. The pharmaceutical composition for use according to any of items 1 to 3, wherein the silicon hydrogel contact lens comprises a silicone hydrogel selected from the group of silicone hydrogels consisting of Balafilcon A, comfilcon A, efrofilcon A, enfilcon, galyfilcon A, lotrafilcon A, lotrafilcon B, narafilcon B, senofilcon A, somofilcon A and sifilcon A.

9. The pharmaceutical composition for use according to any of items 1 to 8, wherein the composition is administered topically to the surface of the eye of the individual after the contact lens has been removed from the eye of the individual.

10. The pharmaceutical composition for use according to any of items 1 to 9, wherein the disease or condition related to the ocular surface of an eye of the individual is associated with contact lens wear.

11. The pharmaceutical composition for use according to any of items 1 to 10, wherein the disease or condition related to the ocular surface of an eye of the individual is dryness associated with continued contact lens wear.
12. The pharmaceutical composition for use according to any of items 1 to 9, wherein the disease or condition related to the ocular surface of an eye of the individual is selected from keratoconjunctivitis sicca (DED) and/or meibomian gland dysfunction (MGD) and/or symptoms associated therewith.
13. The pharmaceutical composition for use according to any of items 1 to 9, wherein the disease or condition related to the ocular surface of an eye of the individual is EOD dryness.
14. The pharmaceutical composition for use according to items 1 to 13, wherein the disease or condition related to the ocular surface of an eye of the individual is contact lense related EOD dryness.
15. The pharmaceutical composition for use according to any of items 10 to 12, wherein the individual suffers concomitantly from a disease or condition defined in any of the items 10 to 12 and from a disease or condition defined in any of the items 13 to 14.
16. A kit comprising a pharmaceutical composition for use according to any of items 1 to 15, a container for holding said composition, means for dispensing said composition to the eye of the individual or patient and optionally instructions on how to use and apply said composition when wearing contact lenses.
17. A method for treating treatment or prevention of a disease or condition relating to an ocular surface of an eye of an individual, wherein the individual is a contact lens wearer, comprising administering a pharmaceutical composition essentially consisting of 1-perfluorohexyl-octane (F6H8) topically to a surface of the eye of the individual after the contact lens has been removed from the eye, and wherein the contact lens is a hydrogel contact lens or a silicone hydrogel contact lens.
18. The method according to item 17, wherein the contact lens is a hydrogel contact lens.
19. The method according to items 17 or 18, wherein the hydrogel contact lens comprises a plastic material selected from the of the group consisting of: Acofilcon A; acofilcon B; alphafilcon A; altraficon A; bufilcon A; crofilcon; deltafilcon A; dimefilcon A; droxifilcon A; epsifilcon A; etafilcon A; focofilcon A; hefilcon A & B; hefilcon C; hilafilcon B; hioxifilcon A; hioxifilcon B; hioxifilcon D; isofilcon; lidofilcon A; lidofilcon B; mafilcon; methafilcon A, B; nelfilcon A; nescofilcon A; netrafilcon A; ocufilcon A; ocufilcon B; ocufilcon C; ocufilcon D; ocufilcon E; ocufilcon F; ofilcon A; omafilcon A; perfilcon A; phemfilcon A; phenfilcon A; polymacon; scafilcon A; surfilcon A; tefilcon; tetrafilcon A; tetrafilcon B; vasurfilcon A; vifilcon A; and xylofilcon A.
20. The method according to item 17, wherein the contact lens is a silicone hydrogel contact lens.
21. The method according to item 17 or 20, wherein the silicon hydrogel contact lens comprises a silicone hydrogel selected from the group of silicone hydrogels consisting of Balafilcon A, comfilcon A, efrofilcon A, enfilcon, galyfilcon A, lotrafilcon A, lotrafilcon B, narafilcon B, senofilcon A, somofilcon A and sifilcon A.
22. The method according to any of items 17 to 21, wherein the disease or condition related to the ocular surface of an eye of the individual is associated with contact lens wear.
23. The method according to any of the items 17 to 22, wherein the disease or condition related to the ocular surface of an eye of the individual is dryness associated with continued contact lens wear.
24. The method according to any of items 17 to 23, wherein the disease or condition related to the ocular surface of an eye of the individual is EOD dryness.
25. The method according to items 23 or 24, wherein the disease or condition is characterized by dryness that increases from insertion to removal of the contact lens.
26. The method according to any of the items 17 to 25, wherein the method is effective in reducing discomfort associated with contact lens wear, preferably with prolonged contact lens wear.
27. The method according to any of the items 17 to 26, wherein the method is effective in ameliorating and/or reducing dryness after, before and during contact lens wear.
28. The method according to any of the items 17 to 27, wherein the method is effective in ameliorating and/or reducing dryness after, before and during contact leans wear.

The following examples serve to illustrate the present invention without, however, limiting it in any respect.

EXAMPLES

Example 1: Material Compatibility Testing (I)

A typical hydrogel contact lens fabricated from hydrophilic plastic material (SofLens® 38, Bausch & Lomb) was investigated for material compatibility with semifluorinated alkanes, namely 1-perfluorobutyl-pentane (F4H5), and 1-perfluorohexyl-octane (F6H8). Herein, a variety of lens powers was tested, in order to include high minus and high plus powers as these represent the extremities of lens thickness. Table 1 summarizes the number of SofLens® test lenses that were used for the study:

TABLE 1

| Lens Parameters | F4H5 (100%) | F6H8 (100%) | Control (Saline) |
| --- | --- | --- | --- |
| High minus power (e.g. −10.00) | 3 | 3 | 3 |
| High plus power (e.g. +8.00), | 3 | 3 | 3 |
| Plano lenses (approx. no power) | 10 | 10 | 10 |

For testing material compatibility, each contact lens was first placed into vials containing saline solution and allowed to equilibrate for at least 24 hours. At this stage, all lenses were evaluated for baseline data, including lens diameter (TD), back vertex power (BVP) and physical appearance.

Once the baseline data (see Table 2 below) was determined for each contact lens, the content within the vials was changed to either one of the two the test products (F4H5, F6H8) or fresh saline if the lens was acting as a control. The contact lenses were immersed for a period of 7 days within the vials filled with F4H5, F6H8 or saline. This scenario represents a worst-case exposure of the semifluorinated alkane to a lens as the contact was undiluted by tear exchange. Afterwards, the test lenses were removed from the vials, rinsed with saline and were re-analyzed to determine if they were still within the appropriate specifications and tolerances as laid out in ISO 18369-2:2006. Light transmission and mechanical properties were also determined for SFA-exposed and control lenses.

TABLE 2

Measured Lens Parameters for Soflens ® 38 Control Lenses

| CONTROL (SALINE) | Starting Parameters | | | Final Parameters (1 week) | | |
|---|---|---|---|---|---|---|
| Lens No | Diameter | BCOR | BVP | Diameter | BCOR | BVP |
| SOFLENS ® 38: 8.40/14.0/−1.00 (PLANO) Batch No: Y31908444 | | | | | | |
| 1 | 13.90 | 8.10 | −1.00 | 13.90 | 8.10 | −1.00 |
| 2 | 13.90 | 8.10 | −1.00 | 13.90 | 8.10 | −1.00 |
| 3 | 13.90 | 8.10 | −1.00 | 13.90 | 8.10 | −1.00 |
| 4 | 13.90 | 8.10 | −1.00 | 13.90 | 8.10 | −1.00 |
| 5 | 13.90 | 8.10 | −1.00 | 13.90 | 8.10 | −1.00 |
| 6 | 13.90 | 8.10 | −1.00 | 13.90 | 8.10 | −1.00 |
| 7 | 13.90 | 8.10 | −1.00 | 13.90 | 8.05 | −1.00 |
| 8 | 13.90 | 8.10 | −0.87 | 13.90 | 8.10 | −1.00 |
| 9 | 13.90 | 8.10 | −1.00 | 13.90 | 8.10 | −1.00 |
| 10 | 13.90 | 8.10 | −0.87 | 13.90 | 8.10 | −0.87 |
| SOFLENS ® 38: 8.40/14.0/4.00 (PLUS) Batch No: Y31903842 | | | | | | |
| 1 | 13.80 | 8.00 | 3.75 | 13.80 | 8.00 | 3.87 |
| 2 | 13.80 | 7.95 | 3.75 | 13.80 | 7.95 | 3.75 |
| 3 | 13.75 | 7.95 | 3.87 | 13.80 | 8.00 | 3.87 |
| SOFLENS ® 38: 8.40/14.0/−9.00 (MINUS) Batch No: Y21909670 | | | | | | |
| 1 | 14.00 | 8.00 | −9.00 | 14.00 | 8.00 | −9.00 |
| 2 | 14.05 | 8.05 | −9.00 | 14.00 | 8.05 | −9.00 |
| 3 | 14.00 | 8.00 | −9.00 | 14.00 | 8.05 | −9.00 |

Test Parameters (a) Lens Diameter (TD=Total Diameter)

The total diameter of the soft hydrogel contact lenses was measured using the projection comparator method as per ISO 18369-3:2006. The projection system was capable of measuring to ±0.05 mm over a range of 0 mm to 17 mm. The scale of the screen represents a linear magnification of at least ×15 and permitted measurement accuracy of 0.05 mm for the contact lens diameter. The diameter of the lens was taken from a marked glass scale (similar to a microscope graticule) under the lens within the support, which is projected onto the screen. Hydrogel lenses were equilibrated at a temperature of 20° C.±0.5° C. and the projection comparator was also maintained at a temperature of 20° C. The contact lens was placed on the support which was then filled with saline which is also maintained at 20° C.±0.5° C.

(b) Back Vertex Power (BVP)

The back vertex power of both soft and rigid contact lenses were determined in air by the use of a focimeter as per ISO 18369-3:2006. The focimeter was modified with a contact lens support so that the contact lens rests on a supporting ring. The lenses were equilibrated prior to measurement and the focimeter and support are kept at 20° C. The contact lens was placed with its posterior surface against the contact lens support to properly position the back vertex as the reference point for measurement. It is important that the back vertex be centered in the pupil of the lens stop and lens surface be free of debris or solution. Therefore, any surface liquid should be removed, particularly for hydrogel lenses immediately prior to measurement.

(c) Physical Appearance

Whilst subject to the various lens parameter measurements, the lenses were also examined visually to ensure no unusual physical changes have occurred during the testing protocol.

(d) Radius of Curvature—Sagittal Depth

Sagittal depth is the distance from the vertex of the contact lens surface to a chord drawn across the surface at a known diameter. For the determination of the sagittal depth of the back optic zone, the contact lens was rested concave side down against a circular contact lens support of fixed outside diameter. The spherometer projects the profiles of the contact lens, lens support and probe onto a screen. The projection system has a magnification of at least 10× and enables the lens, lens support and probe to be focused together. The operator ensured that the contact lens was centered on the support so that the probe approaches along the lens axis, and finally just touches the back vertex of the lens. This was the endpoint required to obtain a measurement value. The distance traveled by a solid mechanical probe from the plane of the lens support to the lens back surface vertex is the sagittal depth.

(e) Visible Light Transmission

The light transmission properties of a polymer are crucial to its success in an ophthalmic application. The light transmission properties of a contact lens were measured using the procedure outlined in ISO 18369-3:2006. The measurement was performed using a spectrophotometer that is fully integrating and can provide a light transmittance value over a range of wavelengths. The instrument must have a bandwidth of 10 nm or less throughout the measurement range. The measurement of transmittance of contact lenses was performed in saline solution. Thus, the measured value represented the performance of the lens in-vivo by simulating light losses due to reflection at the lens/tear layer interface by a lens/saline solution interface.

Contact lenses and saline solution have similar densities. Therefore, a special cuvette is helpful for positioning the contact lens perpendicular to the incident parallel beam during the measurement. The contact lens was positioned into a cuvette which is able to keep the lens in a fixed position at the exact height that the incident beam passes through the cuvette. The lens was held in place sufficiently that it does not float during the measurement.

The measurement was performed with the contact lens in a fully hydrated state whilst immersed in saline. The parallel incident beam had a diameter of approximately 6 mm. The measurement was performed between the wavelengths of 380-780 nm, which covers the entire visible spectrum. It is also possible to investigate the ability of the material to absorb UV light if a UV absorber is present in the material. This was achieved by expanding the measurement range to 200-780 nm thus including the UV range of the electromagnetic spectrum.

(f) Mechanical Properties

Knowledge of the mechanical properties of a material provides important information in the selection of suitable applications. A material must have the required properties to function adequately and must be durable enough for the expected product lifetime. In the case of soft contact lenses, it has been considered that modulus contributes greatly to the success of a material. However, it is also important for a material to have sufficient durability to allow the lens to be handled and cleaned if necessary.

The mechanical properties were determined by tensile testing of the material through the use of a tensiometer. Samples were held under tension and the force applied to the sample is gradually increased until the sample breaks. The tensile strength is the load at break while the elongation at break is the extension of the sample at the point of breaking. The modulus of elasticity was determined from a graphical plot of stress vs. strain over the elastic region of the curve. Values for a range of other properties can be determined using this form of testing.

Test specimens of the required geometry were produced or cut from samples of the material. The thickness of the sample was measured prior to the start of the testing using a micrometer. It is important to accurately know the cross-sectional area of the sample to enable correct calculation of the material properties. A number of parameters can be varied depending on the type of sample being measured. These include the speed of movement of the extension of the sample, the length of the sample and the distance between the clamping jaws at the start of the test, as well as a range of other parameters that define the precise operation of the testing procedure.

The type of sample being evaluated will dictate the size of the test piece being investigated and this in turn will determine the testing geometries employed. For example, when evaluating actual contact lens samples the specific lens design will result in a sample with a variation in cross-sectional area. The situation is further complicated by the intersections of curves that result in thinner regions as you pass from the center to the edge of the lens. To overcome these issues changes in the jaw separation can be used so that the thickness of the test sample is relatively constant, typically found in the centre of the contact lens.

Each sample was placed in the jaws of the equipment ensuring that the sample was positioned correctly. When measuring hydrophilic materials, it is important to ensure that the sample remains hydrated for the duration of the test to ensure representative results are obtained. This process was repeated until the required number of acceptable results was obtained in order to calculate an appropriate average value for each property.

Lens Tolerances (ISO 18369-2:2006)

The tolerances for soft contact lenses are detailed in ISO 18369-2:2006 and those of interest for a solution compatibility study are

| Total Diameter | ±0.20 mm |
| Base Curve Optical Radius (BCOR) | ±0.20 mm |
| Back Vertex Power (BVP) | ±0.25 Dioptre |

Results

When lenses were initially placed in the test products (F4H5, F6H8), they were observed to curl up upon themselves, relatively instantaneously. This may suggest the surface of the lenses, being relatively hydrophilic, tends to minimize its interaction with the relatively hydrophobic solutions of the test products. Over a period of 24 or more hours, the lenses appeared to open up to some degree but they did not appear completely relaxed as they were when observed in saline.

(a) Lens Parameters

F4H5: The Soflens® 38 Lenses handled differently after storing in F4H5 compared to typical handling in saline. During storage in the compound each lens became folded, with the lens surfaces material sticking to itself. When placed in the wet cell for measurement, the lenses could be unfolded and returned to their original spherical shape. There wasn't any change to the parameters of all three power variants (see Table 3 below). The only noticeable difference was the handling of the lenses and the fact they stuck together when stored.

TABLE 3

Measured Lens Parameters for Soflens ® 38 Lenses exposed to F4H5

| F4H5 | Starting Parameters | | | Final Parameters (1 week) | | |
|---|---|---|---|---|---|---|
| Lens No | Diameter | BCOR | BVP | Diameter | BCOR | BVP |
| SOFLENS ® 38: 8.40/14.0/−1.00 (PLANO) Batch No: Y31908444 | | | | | | |
| 1 | 13.90 | 8.10 | −1.00 | 13.90 | 8.05 | −1.00 |
| 2 | 13.90 | 8.10 | −1.00 | 13.90 | 8.05 | −1.00 |
| 3 | 13.90 | 8.10 | −1.00 | 13.90 | 8.10 | −1.00 |
| 4 | 13.90 | 8.10 | −1.00 | 13.90 | 8.10 | −1.00 |
| 5 | 13.90 | 8.10 | −1.00 | 13.90 | 8.05 | −1.00 |
| 6 | 13.90 | 8.10 | −1.00 | 13.90 | 8.05 | −1.00 |
| 7 | 13.90 | 8.10 | −1.00 | 13.90 | 8.10 | −1.00 |
| 8 | 13.90 | 8.10 | −1.00 | 13.90 | 8.10 | −1.00 |
| 9 | 13.90 | 8.10 | −1.00 | 13.90 | 8.10 | −1.00 |
| 10 | 13.90 | 8.10 | −1.00 | 13.90 | 8.10 | −1.00 |
| SOFLENS ® 38: 8.40/14.0/4.00 (PLUS) Batch No: Y31903842 | | | | | | |
| 1 | 13.90 | 8.00 | 4.00 | 13.90 | 8.05 | 4.00 |
| 2 | 13.80 | 8.00 | 4.00 | 13.80 | 8.00 | 4.00 |
| 3 | 13.80 | 8.00 | 4.00 | 13.85 | 8.05 | 4.00 |
| SOFLENS ® 38: 8.40/14.0/−9.00 (MINUS) Batch No: Y21909670 | | | | | | |
| 1 | 14.00 | 8.00 | −8.87 | 14.00 | 8.00 | −9.00 |
| 2 | 14.00 | 8.00 | −9.00 | 14.00 | 7.95 | −9.00 |
| 3 | 14.00 | 8.00 | −9.00 | 14.00 | 8.00 | −8.87 |

F6H8:

The Soflens® 38 lenses also became folded when stored in the F6H8, with the material sticking to itself. The lenses were placed in the ultrasonic bath to remove the excess oily compound. It was then possible to unfold the lens to measure the Base Curve Optical Radius (BCOR) and total diameter (TD). It was not possible to measure the BVP, as the optics were too blurry. When looking through the lenses using florescent light, it could be observed that the surface was rippled. The lenses were then placed into ISO saline for 48 hours and the powers could then be recorded (see Table 4).

Oily compounds were difficult to remove from the lenses and with the exception of the optics, no critical changes were observed for these materials. However, the optical quality improved with storage in standard saline indicating these changes were reversible.

TABLE 4

Measured Lens Parameters for Soflens ® 38 Lenses exposed to F6H8

| F6H8 | Starting Parameters | | | Final Parameters (1 week) | | |
|---|---|---|---|---|---|---|
| Lens No | Diameter | BCOR | BVP | Diameter | BCOR | BVP |
| SOFLENS ® 38: 8.40/14.0/−1.00 (PLANO) Batch No: Y31908444 | | | | | | |
| 1 | 13.90 | 8.10 | −0.87 | 13.90 | 8.15 | −1.00 |
| 2 | 13.90 | 8.10 | −1.00 | 13.90 | 8.10 | −1.00 |
| 3 | 13.90 | 8.10 | −1.00 | 13.90 | 8.10 | −1.00 |
| 4 | 13.90 | 8.10 | −1.00 | 13.90 | 8.10 | −0.87 |
| 5 | 13.90 | 8.10 | −1.00 | 13.90 | 8.10 | −1.00 |
| 6 | 13.90 | 8.10 | −1.00 | 13.90 | 8.10 | −1.00 |
| 7 | 13.90 | 8.10 | −1.00 | 13.90 | 8.15 | −0.87 |
| 8 | 13.90 | 8.10 | −1.00 | 13.90 | 8.10 | −1.00 |
| 9 | 13.90 | 8.10 | −1.00 | 13.85 | 8.15 | −1.00 |
| 10 | 13.90 | 8.10 | −1.00 | 13.90 | 8.15 | −1.00 |

TABLE 4-continued

Measured Lens Parameters for Soflens ® 38 Lenses exposed to F6H8

| F6H8 | Starting Parameters | | | Final Parameters (1 week) | | |
|---|---|---|---|---|---|---|
| Lens No | Diameter | BCOR | BVP | Diameter | BCOR | BVP |
| SOFLENS ® 38: 8.40/14.0/4.00 (PLUS) Batch No: Y31903842 | | | | | | |
| 1 | 13.90 | 8.00 | 4.00 | 13.90 | 8.00 | 4.00 |
| 2 | 13.85 | 8.00 | 4.00 | 13.90 | 8.05 | 4.00 |
| 3 | 13.85 | 8.00 | 4.00 | 13.90 | 8.00 | 4.00 |
| SOFLENS ® 38: 8.40/14.0/−9.00 (MINUS) Batch No: Y31909455 | | | | | | |
| 1 | 14.00 | 7.95 | −8.87 | 14.10 | 8.00 | −9.00 |
| 2 | 14.00 | 8.00 | −8.87 | 14.00 | 8.00 | −8.87 |
| 3 | 14.00 | 8.00 | −8.87 | 14.00 | 8.05 | −8.87 |

(b) Mechanical Properties

The mechanical properties for the Soflens® 38 product showed little difference in the modulus values for the control group (see Table 5 below) compared to either of the test groups (Tables 6 and 7 below, respectively) and this was unsurprising given little interaction was observed in terms of a dimensional change. The test groups appeared to show a slightly reduced elongation to break which consequently also results in a slight decrease in tensile strength, but these changes were relatively minor in nature.

TABLE 5

Mechanical Results for Soflens ® 38 Control Lenses Control Samples

| Nr | Thickness mm | Width mm | E-Modulus MPa | Tensile Strength MPa | Tensile Strength kg/cm$^2$ | Elongation to break % |
|---|---|---|---|---|---|---|
| 1 | 0.03 | 2 | 0.96 | 1.50 | 15.30 | 138.66 |
| 2 | 0.047 | 2 | 0.79 | 2.11 | 21.56 | 221.63 |
| 3 | 0.036 | 2 | 1.35 | 1.63 | 16.62 | 141.88 |
| 4 | 0.034 | 2 | 0.85 | 1.32 | 13.42 | 151.35 |
| 5 | 0.037 | 2 | 0.77 | 2.80 | 28.50 | 217.08 |
| 6 | 0.037 | 2 | 0.92 | 1.84 | 18.79 | 193.13 |
| 7 | 0.039 | 2 | 0.93 | 1.51 | 15.39 | 190.29 |
| Mean | | | 0.94 | 1.82 | 18.51 | 179.15 |
| Std Dev | | | 0.20 | 0.50 | 5.14 | 35.03 |
| % | | | 20.79 | 27.81 | 27.78 | 19.56 |

TABLE 6

Mechanical Results for Soflens ® 38 Lenses exposed to F4H5

| Nr | Thickness mm | Width mm | E-Modulus MPa | Tensile Strength MPa | Tensile Strength kg/cm$^2$ | Elongation to break % |
|---|---|---|---|---|---|---|
| 1 | 0.03 | 2 | 1.01 | 1.62 | 16.48 | 165.27 |
| 2 | 0.045 | 2 | 0.60 | 0.62 | 6.37 | 110.19 |
| 3 | 0.03 | 2 | 1.12 | 0.75 | 7.60 | 92.91 |
| 4 | 0.041 | 2 | 0.98 | 0.83 | 8.43 | 89.85 |
| 5 | 0.031 | 2 | 0.88 | 1.18 | 12.07 | 156.71 |
| 6 | 0.04 | 2 | 1.08 | 1.34 | 13.64 | 156.52 |
| 7 | 0.04 | 2 | 0.70 | 2.53 | 25.77 | 250.37 |
| 8 | 0.03 | 2 | 0.86 | 0.63 | 6.45 | 98.79 |
| 9 | 0.043 | 2 | 0.74 | 0.66 | 6.77 | 119.05 |
| Mean | | | 0.89 | 1.13 | 11.51 | 137.74 |
| Std Dev | | | 0.18 | 0.63 | 6.44 | 51.34 |
| % | | | 20.16 | 56.13 | 55.99 | 37.27 |

TABLE 7

Mechanical Results for Soflens ® 38 Lenses exposed to F6H8

| Nr | Thickness mm | Width mm | E-Modulus MPa | Tensile Strength MPa | Tensile Strength kg/cm$^2$ | Elongation to break % |
|---|---|---|---|---|---|---|
| 1 | 0.037 | 2 | 0.89 | 0.91 | 9.32 | 118.12 |
| 2 | 0.036 | 2 | 1.11 | 2.68 | 27.29 | 238.81 |
| 3 | 0.036 | 2 | 1.14 | 1.33 | 13.53 | 142.73 |
| 4 | 0.031 | 2 | 0.65 | 1.69 | 17.27 | 213.63 |
| 5 | 0.044 | 2 | 0.63 | 1.07 | 10.89 | 163.61 |
| 6 | 0.03 | 2 | 0.70 | 0.63 | 6.39 | 97.23 |
| 7 | 0.034 | 2 | 1.07 | 0.74 | 7.54 | 92.23 |
| 8 | 0.031 | 2 | 1.07 | 1.37 | 14.01 | 154.43 |
| 9 | 0.041 | 2 | 0.98 | 0.76 | 7.74 | 96.40 |
| Mean | | | 0.92 | 1.24 | 12.66 | 146.35 |
| Std Dev | | | 0.21 | 0.64 | 6.54 | 52.54 |
| % | | | 22.49 | 51.63 | 51.62 | 35.90 |

(c) Light Transmission Results

The Soflens® 38 product did not show any significant differences in the light transmission profiles observed for both control and test products (see Table 8).

TABLE 8

Light Transmission Results for Soflens ® 38 Lenses

| Wavelength | Control 1 | Control 2 | F4H5-1 | F4H5-2 | F6H8-1 | F6H8-2 |
|---|---|---|---|---|---|---|
| 380 | 96.68 | 97.68 | 92.87 | 98.20 | 96.96 | 98.12 |
| 390 | 96.82 | 97.78 | 93.80 | 98.20 | 97.22 | 98.26 |
| 400 | 96.93 | 97.82 | 94.11 | 98.22 | 97.22 | 98.42 |
| 410 | 96.94 | 97.85 | 94.32 | 98.25 | 97.27 | 98.50 |
| 420 | 96.95 | 97.96 | 94.47 | 98.30 | 97.32 | 98.56 |
| 430 | 97.07 | 98.09 | 94.58 | 98.42 | 97.39 | 98.61 |
| 440 | 97.22 | 98.26 | 94.75 | 98.54 | 97.53 | 98.69 |
| 450 | 97.38 | 98.41 | 95.00 | 98.66 | 97.67 | 98.78 |
| 460 | 97.45 | 98.50 | 95.30 | 98.74 | 97.77 | 98.86 |
| 470 | 97.53 | 98.63 | 95.44 | 98.84 | 97.87 | 98.97 |
| 480 | 97.59 | 98.60 | 95.59 | 98.90 | 97.96 | 99.03 |
| 490 | 97.60 | 98.70 | 95.79 | 98.90 | 98.02 | 99.50 |
| 500 | 97.67 | 98.65 | 95.90 | 98.90 | 97.99 | 99.84 |
| 510 | 97.67 | 98.65 | 95.88 | 98.91 | 97.99 | 99.73 |
| 520 | 97.50 | 98.59 | 95.94 | 98.85 | 97.98 | 99.42 |
| 530 | 97.35 | 98.50 | 95.94 | 98.86 | 97.88 | 99.18 |
| 540 | 97.40 | 98.34 | 95.88 | 98.73 | 97.77 | 98.96 |
| 550 | 97.26 | 98.22 | 95.93 | 98.68 | 97.64 | 98.54 |
| 560 | 97.13 | 98.07 | 95.92 | 98.61 | 97.49 | 98.37 |
| 570 | 97.12 | 97.97 | 95.91 | 98.48 | 97.37 | 98.38 |
| 580 | 97.15 | 97.86 | 95.85 | 98.32 | 97.22 | 98.44 |
| 590 | 97.00 | 97.81 | 95.82 | 98.23 | 97.00 | 98.30 |
| 600 | 96.93 | 97.68 | 95.74 | 98.09 | 96.83 | 98.14 |
| 610 | 96.87 | 97.78 | 95.76 | 98.12 | 96.84 | 98.11 |
| 620 | 96.95 | 97.88 | 95.91 | 98.15 | 96.85 | 98.15 |
| 630 | 97.02 | 97.92 | 95.87 | 98.04 | 96.85 | 98.10 |
| 640 | 97.01 | 97.90 | 95.73 | 98.00 | 96.76 | 98.01 |
| 650 | 96.95 | 97.97 | 95.87 | 98.04 | 96.78 | 98.06 |
| 660 | 97.07 | 98.07 | 96.08 | 98.22 | 97.02 | 98.30 |
| 670 | 97.22 | 98.35 | 96.58 | 98.37 | 97.38 | 98.62 |
| 680 | 97.40 | 98.66 | 96.86 | 98.64 | 97.67 | 98.81 |
| 690 | 97.42 | 98.87 | 96.98 | 98.80 | 98.04 | 99.38 |
| 700 | 97.61 | 98.99 | 97.20 | 99.00 | 98.23 | 99.48 |
| 710 | 97.84 | 99.18 | 97.35 | 99.05 | 98.43 | 99.60 |
| 720 | 98.01 | 99.12 | 97.51 | 99.16 | 98.47 | 99.62 |
| 730 | 98.05 | 99.17 | 97.50 | 99.19 | 98.57 | 99.86 |
| 740 | 98.14 | 99.19 | 97.71 | 99.30 | 98.51 | 100.42 |
| 750 | 98.07 | 99.29 | 97.71 | 99.28 | 98.56 | 100.63 |
| 760 | 98.13 | 99.21 | 97.95 | 99.43 | 98.46 | 100.49 |
| 770 | 98.32 | 99.23 | 97.95 | 99.64 | 98.61 | 100.29 |
| 780 | 98.35 | 99.28 | 97.66 | 99.77 | 98.54 | 100.17 |

CONCLUSIONS

The SofLens® 38, representing a typical hydrogel contact lens, showed that it is fully compatible with both SFAs tested, namely F4H5 and F6H8. As this was tested by immersing the contact lens in pure SFA for 7 days, this represents a worst-case scenario, as in reality the contact lens placed in the eye would not be completely immersed in SFA, but only partially and the contact lens would be continuously worn less than 168 hours (7 days). Most probably it will be worn only during day time, and less than 7 days. Further, it could be expected that this holds true for compositions comprising F4H5 and/or F6H8 to the extent that these compositions do not contain any further component that is not compatible with such hydrogel contact lens material.

Example 2: Regeneration of the Eye after Contact Lens Wear (EOD Dryness Symptom)

The regeneration of the eye after contact lens wear was tested with silicon hydrogel contact lenses Clariti® 1 day (Coopervision).

Single drops of ~10 µl NovaTears® (consisting of 1-perfluorohexyl-octane) were instilled into the eye sac of both eyes of a test person in the evening after removal of the contact lenses from the eye.

The individual declared that the feeling after instillation of NovaTears® into the eye was very comfortable, silkylike, with no discomfort or dryness feeling. This comfortable feeling was still present on the next morning before the silicon hydrogel contact lenses were again inserted into the eye.

NovaTears®, essentially consisting of 1-perfluorohexyl-octane, is a CE-marked medical device approved in Europe for lubrication of the eye surface, stabilization of the tear film and relief of symptoms associated with dry eye. Importantly, NovaTears® is not indicated for use when wearing contact lenses due to lack of data concerning compatibility of NovaTears® with contact lens material.

Example 3: Simultaneous Wear of Contact Lenses

The concomitant wear of contact lenses with NovaTears® (1-perfluorohexyl-octane) was tested with silicon hydrogel contact lenses (Clariti® 1 day, Coopervision).

Single drops of ~10 µl NovaTears® (1-perfluorohexyl-octane) were instilled into the eye sac of both eyes of a test person before the contact lenses were inserted to the eye. Next, the contact lenses were inserted. The individual declared that he did not feel any discomfort after the contact lenses were inserted into the eye with prior installation of NovaTears®. Further, he did not observe any impairment of vision during the day when wearing the contact lenses. Upon removal of the contact lenses from the eye he did not observe any physical or optical change of the contact lenses.

The invention claimed is:

1. A method of treatment or prevention of a disease or condition relating to an ocular surface of an eye of an individual comprising administering a pharmaceutical composition consisting essentially of 1-perfluorohexyl-octane (F6H8) to the ocular surface of the eye of the individual, wherein the individual is a contact lens wearer, and wherein the contact lens is a hydrogel contact lens or a silicone hydrogel contact lens and the composition is administered topically to a surface of the eye of the individual after the contact lens has been removed from the eye of the individual;

wherein the disease or condition related to the ocular surface of an eye of the individual is EOD dryness.

2. The method of claim 1, wherein the contact lens is a hydrogel contact lens.

3. The method of claim 2, wherein the hydrogel contact lens comprises a plastic material selected from the of the group consisting of: Acofilcon A; acofilcon B; alphafilcon A; altrafilcon A; bufilcon A; crofilcon; deltafilcon A; dimefilcon A; droxifilcon A; epsifilcon A; etafilcon A; focofilcon A; hefilcon A & B; hefilcon C; hilafilcon B; hioxifilcon A; hioxifilcon B; hioxifilcon D; isofilcon; lidofilcon A; lidofilcon B; mafilcon; methafilcon A, B; nelfilcon A; nescofilcon A; netrafilcon A; ocufilcon A; ocufilcon B; ocufilcon C; ocufilcon D; ocufilcon E; ocufilcon F; ofilcon A; omafilcon A; perfilcon A; phemfilcon A; phenfilcon A; polymacon; scafilcon A; surfilcon A; tefilcon; tetrafilcon A; tetrafilcon B; vasurfilcon A; vifilcon A; and xylofilcon A.

4. The method of claim 1, wherein the contact lens is a silicone hydrogel contact lens.

5. The method of claim 4, wherein the silicon hydrogel contact lens comprises a silicone hydrogel selected from the group of silicone hydrogels consisting of Balafilcon A, comfilcon A, efrofilcon A, enfilcon, galyfilcon A, lotrafilcon A, lotrafilcon B, narafilcon B, senofilcon A, somofilcon A and sifilcon A.

6. The method of claim 1, wherein the disease or condition related to the ocular surface of an eye of the individual is associated with contact lens wear.

7. The method of claim 1, wherein the disease or condition related to the ocular surface of an eye of the individual is dryness associated with continued contact lens wear.

8. The method of claim 1, wherein the disease or condition is characterized by dryness that increases from insertion to removal of the contact lens.

9. A kit comprising a pharmaceutical composition consisting essentially of 1-perfluorohexyl-octane (F6H8), a container for holding said composition, a means for dispensing said composition to the eye of the individual or patient and optionally instructions on how to use and apply said composition when wearing contact lenses.

* * * * *

UNITED STATES PATENT AND TRADEMARK OFFICE
CERTIFICATE OF CORRECTION

PATENT NO. : 11,278,503 B2  
APPLICATION NO. : 16/612961  
DATED : March 22, 2022  
INVENTOR(S) : Bernhard Günther et al.

Page 1 of 1

It is certified that error appears in the above-identified patent and that said Letters Patent is hereby corrected as shown below:

In the Specification

Column 7, Line 51-52, "water content $\geq 250\%$" should be changed to – water content $\geq 50\%$ –

Signed and Sealed this  
Thirteenth Day of September, 2022

Katherine Kelly Vidal  
*Director of the United States Patent and Trademark Office*